(12) United States Patent
Willis et al.

(10) Patent No.: US 8,632,979 B2
(45) Date of Patent: Jan. 21, 2014

(54) METHODS FOR DETERMINING AGENTS THAT TREAT OR PREVENT OBESITY AND/OR OBESITY RELATED DISEASES AND METHODS FOR TREATMENT THEREWITH

(75) Inventors: Ian M. Willis, New Rochelle, NY (US); Nouria Hernandez, St Sulpice (CH); Wassim Hodroj, Bures sur Yvette (FR)

(73) Assignees: Albert Einstein College of Medicine of Yeshiva University, Bronx, NY (US); University of Lausanne, Lausanne (CH)

( * ) Notice: Subject to any disclaimer, the term of this patent is extended or adjusted under 35 U.S.C. 154(b) by 61 days.

(21) Appl. No.: 13/298,370

(22) Filed: Nov. 17, 2011

(65) Prior Publication Data

US 2012/0128690 A1     May 24, 2012

Related U.S. Application Data

(60) Provisional application No. 61/415,984, filed on Nov. 22, 2010.

(51) Int. Cl.
*G01N 33/566* (2006.01)
*C12Q 1/68* (2006.01)
*A61P 1/16* (2006.01)
*C12Q 1/02* (2006.01)

(52) U.S. Cl.
USPC ........... 435/6.13; 435/7.1; 435/29; 424/158.1

(58) Field of Classification Search
None
See application file for complete search history.

(56) References Cited

U.S. PATENT DOCUMENTS

| | | | | |
|---|---|---|---|---|
| 5,371,077 | A * | 12/1994 | Schroepfer et al. | 514/179 |
| 5,604,113 | A * | 2/1997 | White et al. | 435/29 |
| 2004/0209942 | A1* | 10/2004 | Li | 514/432 |
| 2006/0258569 | A1* | 11/2006 | McTavish | 514/8 |
| 2008/0275076 | A1* | 11/2008 | Holm et al. | 514/291 |

OTHER PUBLICATIONS

Bolon, 2004, Basic & Clinical Pharmacology & Toxicology, vol. 95, pp. 154-161.*
Vickers, 2012, Neuropharmacology, vol. 63, pp. 124-131.*
Wei, 2010, Nucleus, vol. 1, issue 2, pp. 162-165.*
Loos, 2012, Best Practice and Clinical Endocrinology and Metabolism, vol. 26, pp. 211-226.*
Friedman, 2009, Nature, vol. 459, pp. 340-342.*
Friedman, 2000, Nature, vol. 404, pp. 632-634.*
Michels, 2010, Molecular and Cellular Biology, vol. 30, issue 15, pp. 3749-3757.*
Reina, 2006, PLoS One, Issue 1, e134, pp. 1-10.*
Schuler, 2001, Biochemical Society Transactions, vol. 29, part 6, pp. 684-688.*
Johnson, 2007, Molecular Cell, vol. 26, pp. 367-379.*
Voskoglou-Nomikos, 2003, Clinical Cancer Research, vol. 9, pp. 4227-4239.*
White, 2004; European Journal of Cancer, vol. 40, pp. 21-27.*
Cabart, P., et al., entitled "Facilitated Recycling Protects Human RNA Polymerase III from Repression by Maf1 in Vitro," The Journal of Biological Chemistry, vol. 283, No. 52, pp. 36108-36117, Dec. 26, 2008.
Desai, N., et al., entitled "Two Steps in Maf1-dependent Repression of Transcription by RNA Polymerase III," The Journal of Biological Chemistry, vol. 280, No. 8, pp. 6455-6462, Feb. 25, 2005.
Johnson, S., et al., entitled "Mammalian Maf1 Is a Negative Regulator of Transcription by All Three Nuclear RNA Polymerases," Molecular Cell 26, pp. 367-379, May 11, 2007.
Lee, J., et al., entitled "Regulation of RNA Polymerase III Transcription Involves SCH9-dependent and SCH9-independent Branches of the Target of Rapamycin (TOR) Pathway," The Journal of Biological Chemistry, vol. 284, No. 19, May 8, 2009, pp. 12604-12608.
Moir, R., et al., entitled "Protein Kinase A Regulates RNA Polymerase III transcription through the nuclear localization of Maf1," PNAS, pp. 15044-15049, Oct. 10, 2006, vol. 103, No. 41.
Rollins, J., et al., entitled "Human Maf1 Negatively Regulates RNA Polymerase III transcription via the TFIIB family members Brf1 and Brf2," International Journal of Biological Sciences, May 1, 2007, vol. 3, pp. 292-302.
Upadhya, R., et al., entitled "Maf1 is an Essential Mediator of Diverse Signals that Repress RNA Polymerase III Transcription," Mol Cell., Dec. 2002;10(6), pp. 1489-1494, Abstract Only.
Willis, I., et al., entitled "Genetic Interactions of MAF1 Identify a Role for Med20 in Transcriptional Repression of Ribosomal Protein Genes," PLoS Genetics, vol. 4, Issue 7, Jul. 2008, pp. 1-10.

* cited by examiner

*Primary Examiner* — Joanne Hama
*Assistant Examiner* — Ian Dang
(74) *Attorney, Agent, or Firm* — Amster Rothstein & Ebenstein LLP

(57) ABSTRACT

The present invention provides methods for determining a putative agent that treats or prevent obesity and/or obesity related diseases comprising contacting cells with the putative agent and measuring the activity and/or level of Maf1 and/or the activity and/or level of KIAA1875. The present invention also provides the agent identified by the methods herein and methods of treating or preventing obesity and/or obesity related diseases in a subject comprising administering to the subject a therapeutically effective amount of an agent that inhibits or downregulates Maf1 and/or activates or upregulates KIAA1875.

17 Claims, 20 Drawing Sheets

A

B

A

B

METHODS FOR DETERMINING AGENTS THAT TREAT OR PREVENT OBESITY AND/OR OBESITY RELATED DISEASES AND METHODS FOR TREATMENT THEREWITH

CROSS-REFERENCE TO RELATED APPLICATION

This application claims the benefit of U.S. Provisional Patent Application No. 61/415,984, filed Nov. 22, 2010, the content of which is herein incorporated by reference.

STATEMENT OF GOVERNMENT SUPPORT

This invention was made with government support under grant numbers DK041296 and GM085177 awarded by the National Institutes of Health, U.S. Department of Health and Human Services. The government has certain rights in the invention.

FIELD OF THE INVENTION

The present invention relates generally to methods for determining agents that treat or prevent obesity and to methods for treating or preventing obesity and/or obesity related diseases.

BACKGROUND OF THE INVENTION

The worldwide incidence of obesity has risen dramatically in recent years. In the U.S., one third of adults are obese and two thirds are overweight. The excessive increase in body weight in the population is a major public health concern owing to its contribution to a diverse array of medical conditions including metabolic syndrome, insulin resistance, type 2 diabetes, dyslipidemia, cardiovascular disease and non-alcoholic fatty liver disease. There are few pharmacological therapies to treat or provide protection against the development of obesity.

Current treatment for obesity includes combinations of the following: diet, exercise, behavior modification, weightloss drugs and in extreme cases, gastrointestinal surgery. Of the few medications that are available to treat obesity, phentermine is approved only for short term use, sibutramine is approved for longer term use but may cause an increase in blood pressure and orlistat, which blocks the absorption of dietary fat, has unpleasant side effects (greasy stool).

The Maf1 protein is an essential mediator of transcriptional repression by RNA polymerase III in budding yeast. The protein resides at the downstream end of multiple nutrient and stress signaling pathways that control cell growth by coordinately regulating ribosome and tRNA synthesis. Maf1 functions to integrate the responses from these diverse pathways to balance the synthesis of tRNAs, 5S rRNA and other small non-coding RNAs with the needs of the cell. Maf1 is post-translationally regulated and interacts directly with components of the RNA polymerase III transcription machinery.

Maf1 orthologs are found in all eukaryotes and the regulatory function of the protein, as determined in yeast, is conserved in human cells. Human Maf1 is ubiquitously expressed and like its yeast counterpart, is required for maximal repression of RNA polymerase III transcription following inhibition of TOR signaling (e.g. by rapamycin) or in response to genotoxic stress. The phospho-regulation of Maf1 and its interactions with components of the RNA polymerase III transcription machinery are also conserved between yeast and humans. In contrast to yeast, the repressive function of Maf1 in mammals is not limited to the RNA polymerase III system but affects all three nuclear RNA polymerases. Studies in glioblastoma cells have shown that Maf1 directly regulates a subset of RNA polymerase II promoters, including the gene encoding the TATA box-binding protein TBP. By altering the cellular concentration of TBP, Maf1 indirectly affects the transcription of ribosomal RNA genes by RNA polymerase I and may indirectly affect the expression of other genes whose transcription by RNA polymerase II is limited by TBP.

The current invention addresses the need for a pharmacological therapy to treat or prevent obesity and/or obesity related diseases.

SUMMARY OF THE INVENTION

The present invention provides a method for determining a putative agent that treats or prevents obesity and/or obesity related diseases, the method comprising contacting cells with the putative agent and measuring the activity and/or level of Maf1 and/or the activity and/or level of KIAA1875, wherein inhibition or downregulation of Maf1 and/or activation or upregulation of KIAA1875 in the presence of the putative agent indicates that the putative agent is a candidate for treating or preventing obesity and/or obesity related diseases, and wherein lack of inhibition or downregulation of Maf1 and/or activation or upregulation of KIAA1875 in the presence of the putative agent is indicative that the putative agent is not a candidate for treating or preventing obesity and/or obesity related diseases.

The present invention further provides the agent identified by contacting cells with the putative agent and measuring the inhibition or downregulation of Maf1 and/or the activation or upregulation of KIAA1875.

The present invention also provides a method of treating or preventing obesity and/or obesity related diseases in a subject, the method comprising administering to the subject a therapeutically effective amount of an agent that inhibits or downregulates Maf1 and/or activates or upregulates KIAA1875.

The present invention additionally provides the use of an agent that inhibits or downregulates Maf1 and/or activates or upregulates KIAA1875 to treat or prevent obesity and/or obesity related diseases in a subject. The present invention also provides the use of an agent that inhibits or downregulates Maf1 and/or activates or upregulates KIAA1875 for use in treating or preventing obesity and/or obesity related diseases in a subject.

DETAILED DESCRIPTION OF THE INVENTION

Figure 1A:
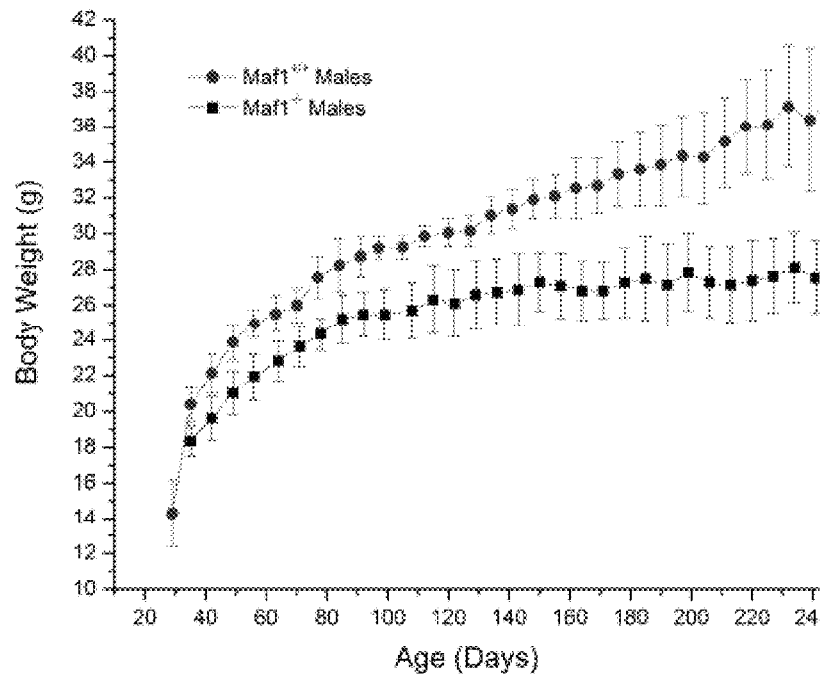
FIG. 1A-1B. Body weight of 8 wt (circles) and 8 Maf1 KO (squares) male mice (A) and 20 wt (grey squares) and 14 Maf1 KO (black squares) female mice (B) fed a breeding diet (20% fat) as a function of age.

The present invention provides a method for determining a putative agent that treats or prevents obesity and/or obesity related diseases, the method comprising contacting cells with the putative agent and measuring the activity and/or level of Maf1 and/or the activity and/or level of KIAA1875, wherein inhibition or downregulation of Maf1 and/or activation or upregulation of KIAA1875 in the presence of the putative agent indicates that the putative agent is a candidate for treating or preventing obesity and/or obesity related diseases, and wherein lack of inhibition or downregulation of Maf1 and/or activation or upregulation of KIAA1875 in the presence of the putative agent is indicative that the putative agent is not a candidate for treating or preventing obesity and/or obesity related diseases.

The present invention further provides the agent identified by contacting cells with the putative agent and measuring the inhibition or downregulation of Maf1 and/or the activation or upregulation of KIAA1875.

The present invention also provides a method of treating or preventing obesity and/or obesity related diseases in a subject, the method comprising administering to the subject a therapeutically effective amount of an agent that inhibits or downregulates Maf1 and/or activates or upregulates KIAA1875.

The present invention additionally provides the use of an agent that inhibits or downregulates Maf1 and/or activates or upregulates KIAA1875 to treat or prevent obesity and/or obesity related diseases in a subject. The present invention also provides the use of an agent that inhibits or downregulates Maf1 and/or activates or upregulates KIAA1875 for use in treating or preventing obesity and/or obesity related diseases in a subject.

Maf1 is a conserved repressor of transcription essential for repressing transcription by RNA polymerase III. It is encoded by Maf1. Multiple nutrient and stress signaling pathways converge on Maf1, and Maf1 is known to directly repress RNA polymerase III transcription of multiple RNA polymerase III genes including, for example, tRNA genes and the U6 small nuclear RNA genes. Maf1 also represses RNA polymerase III transcription of protein coding genes such as the genes encoding the TATA box-binding protein (TBP), and indirectly represses RNA polymerase I transcription of the large ribosomal RNAs. Maf1 is highly conserved in eukaryotic cells Inhibiting Maf1 means interfering with the interactions of the Maf1 proteins or proteins in the Maf1 pathways. Downregulating Maf1 means causing a decrease in the production of Maf1 proteins, or proteins in the Maf1 pathway. Measuring the activity and/or level of Maf1 can be done by any means know in the art including measuring the levels of Maf1 protein interactions, presence of Maf1 proteins, production of Maf1 proteins in the cell, and/or Maf1 mRNA expression. The amino acid sequence for human Maf1 protein is as follows: MKLLENSSFE AINSQLTVET GDAHIIGRIE SYSCKMAGDD KHMFKQFCQE GQPHVLEALS PPQTSGLSPS RLSKSQGGEE EGPLSDKCSR KTLFYLI-ATL NESFRPDYDF STARSHEFSR EPSLSWVVNA VNC-SLFSAVR EDFKDLKPQL WNAVDEEICL AECDIYSYNP DLDSDPFGED GSLWSFNYFF YNKRLKRIVF FSCR-SISGST YTPSEAGNEL DMELGEEEVE EESRSRGSGA EETSTMEEDR VPVICI (SEQ ID NO:1) (GENBANK ACCESSION NO: CAG38494.1).

KIAA1875 is a protein encoded by a gene neighboring Maf1. Activating KIAA1875 means increasing the activity of KIAA1875 proteins or proteins in the KIAA1875 pathways. Upregulating KIAA1875 means causing an increase in the production of KIAA1875 proteins, or proteins in the KIAA1875 pathways. Measuring the activity and/or level of KIAA1875 can be done by any means know in the art including measuring levels of KIAA1875 protein interactions, presence of KIAA1875 proteins, production of KIAA1875 proteins, and/or KIAA1875 mRNA expression. The amino acid sequence for human KIAA1875 protein is as follows: EDVPEGPRRG GRPSAATDEP GVTDFRPTAE AHQPP-WGSQP QVPWRPAQPS WRPSFPTLGG GLAVWGPLEL IQACLSPGTP VWGWSLSQPL PQPTGMPPSI PPVPVPVCSE ALSLIHRRRA TSQHLVPKED LDAI-VARDRD LQQLRLGLVV PAAQPPPSWQ QRQEGFD-NYL RLIYGSGLLG MQSGRGSQQW SAGTLRVERE TRDVCAVPQA AHCLARAEVS TAAQTVPTAL SPQDL-GALGQ HFSQSPRVTV PIPPTHRRVH SKASQLLARS SLSHYLGISL DLQLQLEQLR GRTTMALDLP SSHLQCRIPL LPKRWDKEPL SSLRGFFPAT VQPHKH-CLRP ICFPGYVPNS AVLQQMWLNA EPGASQDALW LWRPRPSQAQ WQRKLLQWMG EKPGEEGEED KKEEEEEKED EELDWALASL SPHSNQQLDS WELEDQSAVD WTQEPRRRSC KVARTHPHPW HRHGSLLLDE HYGHLPKFLH FFIYQTWFKK LFPIFS-LQAY PEAGTIEGLA SLLVALLEKT TWVDRVHILQ VLLRLLPNMS SDLQGQLQGL LVHLLNLDQP PSLQDQTQKK FVILALQLLL ACSLESRDVV LELMSY-FLYS PVHCRPELKK LLHGLGLQDP EGFLFKEMMT WVQGPDLDSK AGLRTCCHQK LEDMIQELQE TPSQTSVVSG APTRASVIPS GTSWSASGIF GRLSQVSEVP LMVVSPAEPH SLAPELQAQR MLAP-TRSWGT PQLRLRVLSE TLKSFCLEPE ARLHPAGPAQ LPGEPPPLEE TDWSHSQLLD LGPIDALNFF CEQL-RAQQRS SLQEKAAHPH PPVPYTVAPV PDMVVPPPRE HWYHPILRLQ EAKPQRSARS AMRLRGPMPS RLCAGRTLDG PIRTLKLPLP RVEPQPFPLD WPMP-PRPLPP RLLQPALQRY FLPADADPDT YS (SEQ ID NO:2).

The cells may be located in vivo or in vitro. The cells may be any eukaryotic cell. For example, the cells may be yeast cells or mammalian cells, such as rodent or human cells. The cells may be in vivo in any subject. For example, the subject may be a mammal such as a rodent or a human. When the cells are in vivo, contacting the cells with the putative agent comprises administering the putative agent to the subject. The cells may be any cell type such as, for example, adipocytes, liver cells, or visceral fat tissue.

The activity and/or level of Maf1 and/or activity and/or level of KIAA1875 can be measured by any method known in the art, including, for example, measuring protein or mRNA expression. Protein or mRNA expression can be measured directly or indirectly, including, for example, such methods as immunoblotting, biochemical assay, or RNA analysis. Any method of immunoblotting may be used, for example, Western blot analysis. Any method of RNA analysis known in the art may be used, for example, RT-PCR. Any method of bio-chemical assay known in the art may be used, for example, assaying transcription activity for the increased transcription associated with decreased expression of Maf1; in vitro assay for inhibition of RNA polymerase III; or in vivo assay for expression of Maf1 regulated cells. In another example, measuring activity and/or level of Maf1 and/or activity and/or level of KIAA1875 may comprise measuring cell weight, cell size, cellular lipid levels, cellular glucose clearance, or plasma lipid or cholesterol levels. Weight gain of the cell or the subject may be measured by any method known in the art. Cell size, cellular lipid levels, or glucose clearance in the cell may be measured by any method known in the art and the measurement may be taken on the cells, systemically on the subject, or by measuring cell size, lipid levels, or glucose clearance in the subject's cells. For example, a hyperinsulinemic-euglycemic-clamp test may be performed on the subject to determine glucose clearance. In another example, cell size of the cells or of cells from the subject may be measured microscopically. In yet another example, cellular lipid levels may be measured by histological examination of the cells or cells or cell sections from the subject. Plasma lipid or cholesterol levels may be measured in vivo, directly or indirectly, by any method known in the art, for example, by measuring liver glycogen.

In one example, the cells may be maintained under conditions which (1) result in increased cell weight, increased cell size, cellular lipid buildup, impaired cellular glucose clearance, or increased plasma lipid or cholesterol levels in the absence of a putative agent that inhibits or downregulates Maf1 and/or activates or upregulates KIAA1875 and (2) do not result in increased cell weight, increased cell size, cellular lipid buildup, impaired cellular glucose clearance, or increased plasma lipid or cholesterol levels in the presence of a putative agent that inhibits or downregulates Maf1 and/or activates or upregulates KIAA1875 for a period of time between contacting the cells with the putative agent and measuring the cells. Maintaining cells contacted with a putative agent that inhibits or downregulates Maf1 and/or activates or upregulates KIAA1875 under the abovementioned conditions will not result in increased cell weight, increased cell size, cellular lipid buildup, impaired cellular glucose clearance, or increased plasma lipid or cholesterol levels as compared to the baseline measurement of those cells. Maintaining cells contacted with a putative agent that does not inhibit or downregulate Maf1 and/or activate or upregulate KIAA1875 will result in increased cell weight, increased cell size, cellular lipid buildup, impaired cellular glucose clearance, or increased plasma lipid or cholesterol levels as compared to the baseline measurement of those cells. Maintaining the cells under the abovementioned conditions for a period of time may allow a greater change in cell weight, cell size, cellular lipid levels, impaired cellular glucose clearance, or increased plasma lipid or cholesterol levels in response to a putative agent that inhibits or downregulates Maf1 and/or activates or upregulates KIAA1875. The period of time may be between 3 hours and 12 months. In vivo, the period of time is preferably between 3 weeks and 12 months. In vitro, the period of time is preferably between 3 hours and 3 months.

The conditions which (1) result in increased cell weight, increased cell size, cellular lipid buildup, impaired cellular glucose clearance, or increased plasma lipid or cholesterol levels in the absence of a putative agent that inhibits or downregulates Maf1 and/or activates or upregulates KIAA1875 and (2) do not result in increased cell weight, increased cell size, cellular lipid buildup, impaired cellular glucose clearance, or increased plasma lipid or cholesterol levels in the presence of a putative agent that inhibits or downregulates Maf1 and/or activates or upregulates KIAA1875 may be any known in the art such as, for example, a high fat diet if the cells are located in vivo or a lipid rich medium if the cells are in vitro.

One or more controls may be performed. The cell weight, cell size, cellular lipid levels, cellular glucose clearance, or plasma lipid or cholesterol levels of a control may be compared to a cell contacted with the putative agent to aid determination of whether the putative agent inhibits or downregulates Maf1 and/or activates or upregulates KIAA1875. Any control known in the art may be used. Examples of controls include, but are not limited to: (A) measuring cell weight, cell size, cellular lipid levels, cellular glucose clearance, or plasma lipid or cholesterol levels of Maf1 knockout and/or KIAA1875 upregulated cells, wherein a lack of increased cell weight, increased cell size, cellular lipid buildup, impaired cellular glucose clearance, or increased plasma lipid or cholesterol levels of the cells contacted with the putative agent relative to the control is indicative that the putative agent is a candidate for treating or preventing obesity and/or obesity related diseases and wherein increased cell weight, increased cell size, cellular lipid buildup, impaired cellular glucose clearance, or increased plasma lipid or cholesterol levels of the cells contacted with the putative agent relative to the control is indicative that the putative agent is not a candidate for treating or preventing obesity and/or obesity related diseases; and (B) measuring cell weight, cell size, cellular lipid levels, cellular glucose clearance, or plasma lipid or cholesterol levels of cells in the absence of the putative agent, wherein increased cell weight, increased cell size, cellular lipid buildup, impaired cellular glucose clearance, or increased plasma lipid or cholesterol levels of the control relative to the cells contacted with the putative agent is indicative that the putative agent is a candidate for treating or preventing obesity and/or obesity related diseases and wherein a lack of increased cell weight, increased cell size, cellular lipid buildup, impaired cellular glucose clearance, or increased plasma lipid or cholesterol levels of the control relative to the cells contacted with the putative agent is indicative that the putative agent is not a candidate for treating or preventing obesity and/or obesity related diseases.

The putative agent may be any chemical or biological agent such as a chemical, small compound, polypeptide, protein, protein fragment, aptamer or siRNA. In one example, the putative agent may inhibit or downregulate Maf1. In another example, the putative agent may activate or upregulate KIAA1875. Preferably, the putative agent is membrane-permeable. An aptamer may be a single stranded oligonucleotide or oligonucleotide analog that binds to a particular target molecule, such as a protein. An aptamer may be a protein aptamer which consists of a variable peptide loop attached at both ends to a protein scaffold that interferes with protein interactions. An siRNA, or small interfering RNA, is a double-stranded RNA molecules, 20-25 nucleotides in length. siRNAs can interfere with the expression of specific genes. Transfection may be used to introduce siRNAs into specific cell or tissue types. An antibody is a protein consisting generally of two heavy and two light chains with a small region at the tip of the protein that can bind to different targets, or antigens. Antibodies or antibody fragments can bind to proteins, thereby inhibiting the protein's interactions. Antibodies or antibody fragments may be nonspecific or monospecific, such as monoclonal antibodies. Antibodies or antibody fragments may be natural or may be made by any method known in the art, for example, by fusing myeloma cells with spleen cells for a mouse that has been immunized with a portion of the protein of interest. Antibodies or antibody fragments can be humanized to reduce possible reaction in humans. Antibodies or antibody fragments may be recombinant and may be purified by any method known in the art, for example, antigen-affinity chromatography. In one example, the agent is an aptamer, siRNA, antibody, antibody fragment that specifically binds to the Maf1 protein or a nucleic acid encoding Maf1 protein.

Obesity related diseases include metabolic syndrome, insulin resistance, type 2 diabetes, dyslipidemia, cardiovascular disease, non-alcoholic fatty liver disease, and others. Treating obesity and/or obesity related diseases means affecting inhibiting or attenuating the clinical severity or progression of the subject's obesity and/or obesity related diseases. Preventing obesity and/or obesity related diseases means delaying or forestalling clinical diagnosis of obesity and/or obesity related diseases in a subject. A therapeutically effective amount is an amount that effects a clinically significant change in the symptoms, severity, or progression of the subject's obesity and/or obesity related diseases. A therapeutically effective amount will depend on the subject, the subject's weight, and the method of administration, among others. One of ordinary skill in the art can determine a therapeutically effective amount without undue experimentation.

EXPERIMENTAL DETAILS

1. Methods and Materials
Generation of the Maf1 KO Mice

To generate a conditional Maf1 KO mouse, a vector was designed and Ozgene Pty. Ltd Australia generated the mouse. The mouse Maf1 gene contains 8 exons and 7 introns. The ATG is in the $2^{nd}$ exon and the stop codon is at the beginning of the $8^{th}$ exon. The conditional Maf1 KO mouse has a floxed Maf1 allele with loxP sites within the first intron and in the $8^{th}$ exon, downstream of the stop codon. Upon crossing with mice expressing the Cre recombinase from the Rosa 26 locus, viable and fertile Maf1 KO mice of both sexes were obtained that lack about 2000 bp of genomic DNA. Table 1 shows that this mouse is indeed completely lacking expression of the Maf1 gene.

TABLE 1

Loss of MAF1 expression in MAF1 KO MEFs

| | Ct for MAF1 | Ct β-ACTIN |
|---|---|---|
| KO1 | ND | 20.39 |
| KO2 | ND | 20.37 |
| KO3 | ND | 19.49 |
| KO4 | ND | 19.35 |
| KO5 | ND | 20.2 |
| KO6 | ND | 19.46 |
| WT1 | 23.68 | 18.52 |
| WT2 | 23.56 | 18.26 |
| WT3 | 24.69 | 19.65 |
| WT4 | 24.97 | 20.28 |
| WT5 | 23.9 | 18.64 |
| WT6 | 23.78 | 19.56 |

The Ct values for Maf1 and β-actin mRNA were obtained by RT-PCR with six samples each of Maf1 KO and wild type MEFs.
ND: not detected.

2. Results
Phenotype of the Maf1 KO Mice

The Maf1 KO mice display several striking phenotypes: (I) Young mice appear normal but as they age, they exhibit substantially lower body weights than wild type mice, with a difference of up to 25% in 30 week-old male mice. (II) Maf1 KO mice display a dramatic reduction in adipose tissues. (III) Glycemia and insulinemia are normal in the fed state or after a fasting period of 5 hours. However, after a long fasting period (16 h), Maf1 KO mice become hyperglycemic and hyperinsulinemic. (IV) Maf1 KO mice are resistant to the weight gain normally seen with wild type animals on a very high fat diet. When on a diet containing 60% fat, their weight remains stable and the hyperglycemia after a 16 h fasting period is not, or only slightly, aggravated.

Differences in Weight and Length

Figure 1B:
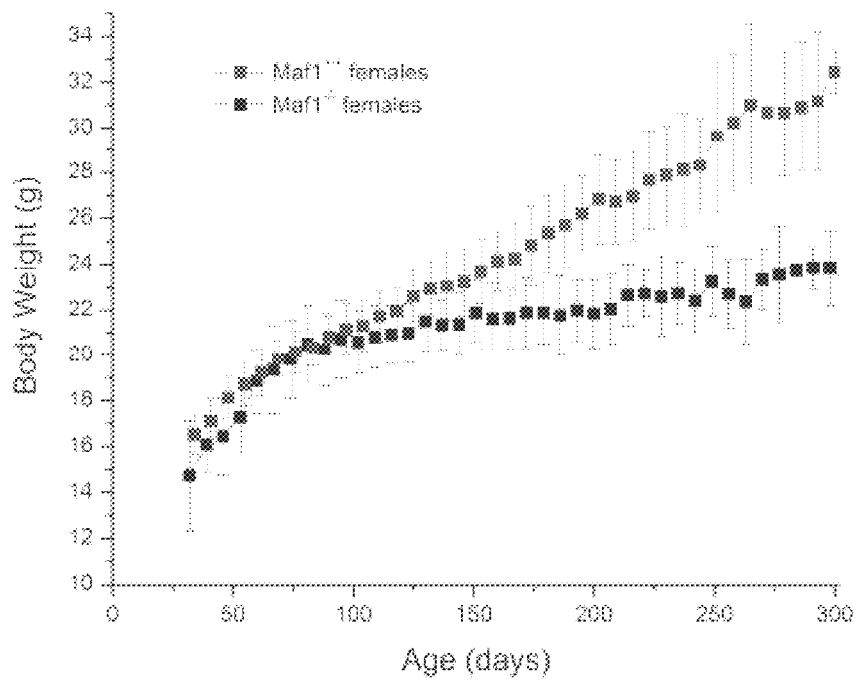
Figure 2:
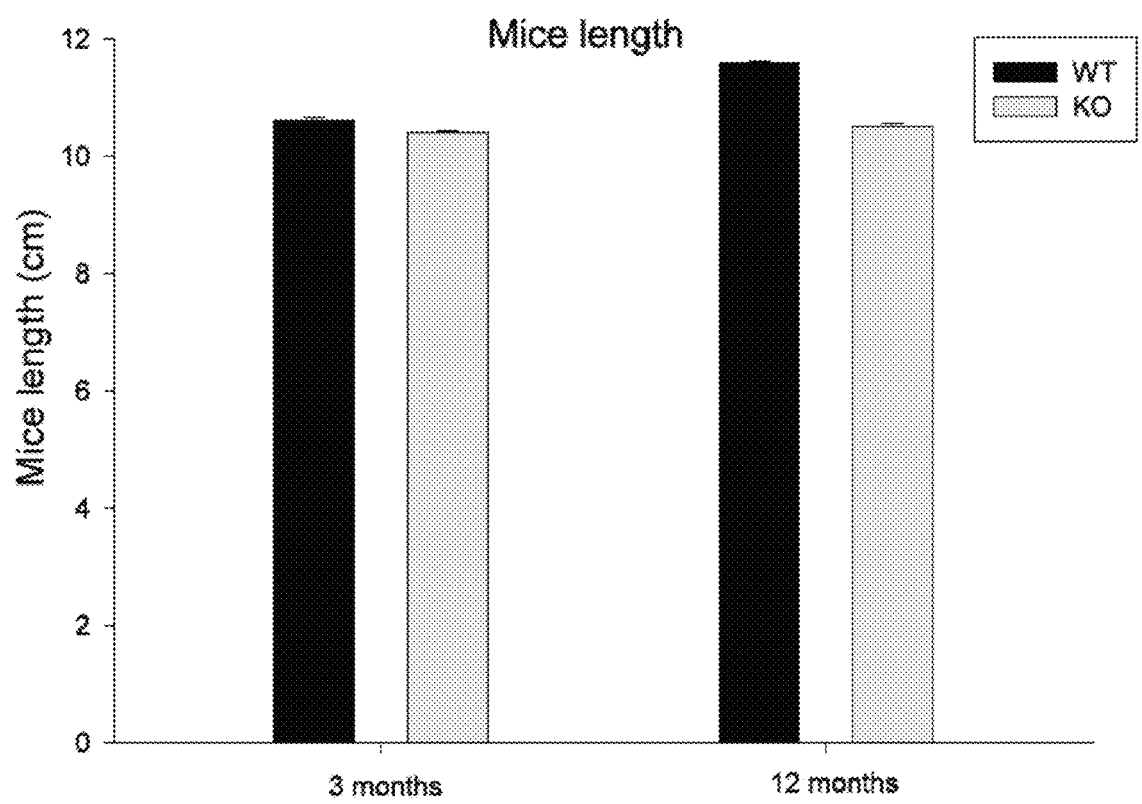
FIG. 2. Body length (anus to nose tip) of 6 wt (black bars) and 6 Maf1 KNO (grey bars) male mice at 3 and 12 months of age as indicated.

Maf1 KO animals show significant deviations in body weight from age-matched wild type animals. From about 5 weeks of age, male Maf1 KO animals are lighter than their wild type counterparts and this difference becomes more pronounced as they age (FIG. 1 (A), 35 days). By the time they reach ~32 weeks of age, the average Maf1 KO male has attained only 75% of the body weight of the average wild type animal (FIG. 1(A), 225 days). Similar body weight differences are seen in females although this takes longer to appear. Wild type and Maf1 KO females are not noticeably different in weight until about 16 weeks of age. However, by the time they are 40 weeks old, Maf1 KO females have grown to only 70% of the body weight of wild type (FIG. 1(B)). As shown in FIG. 2, the Maf1 KO mice are on average 2-3 mm shorter than matched wild type controls at 3 months of age and 11 mm shorter at 12 months. Thus, the Maf1 KO mice are slightly smaller than wild type (~11%) and much lighter (~25%).

Hyperglycemia and Hyperinsulinemia.

Figure 3:
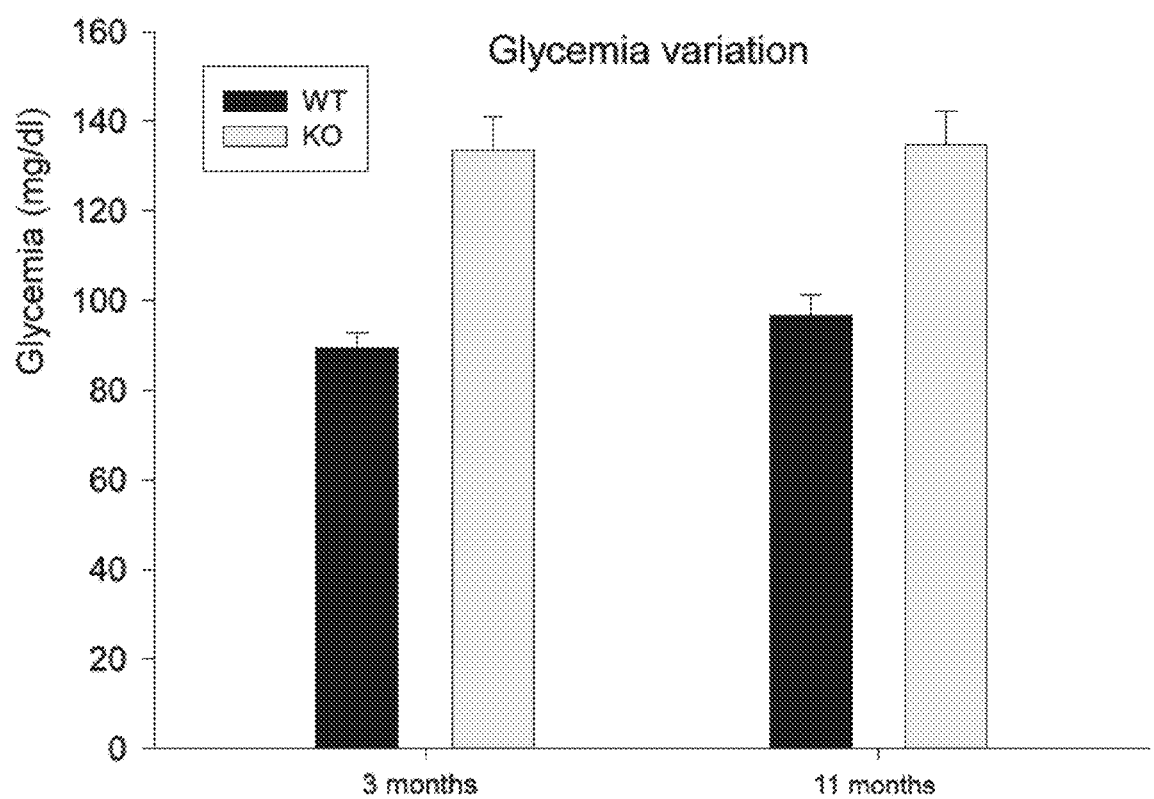
FIG. 3. Gylcemia levels in 12 wt (black bars) and 12 Maf1 KNO (grey bars) male mice after 16 h fasting at 3 and 11 months of age as indicated.
Figure 4:
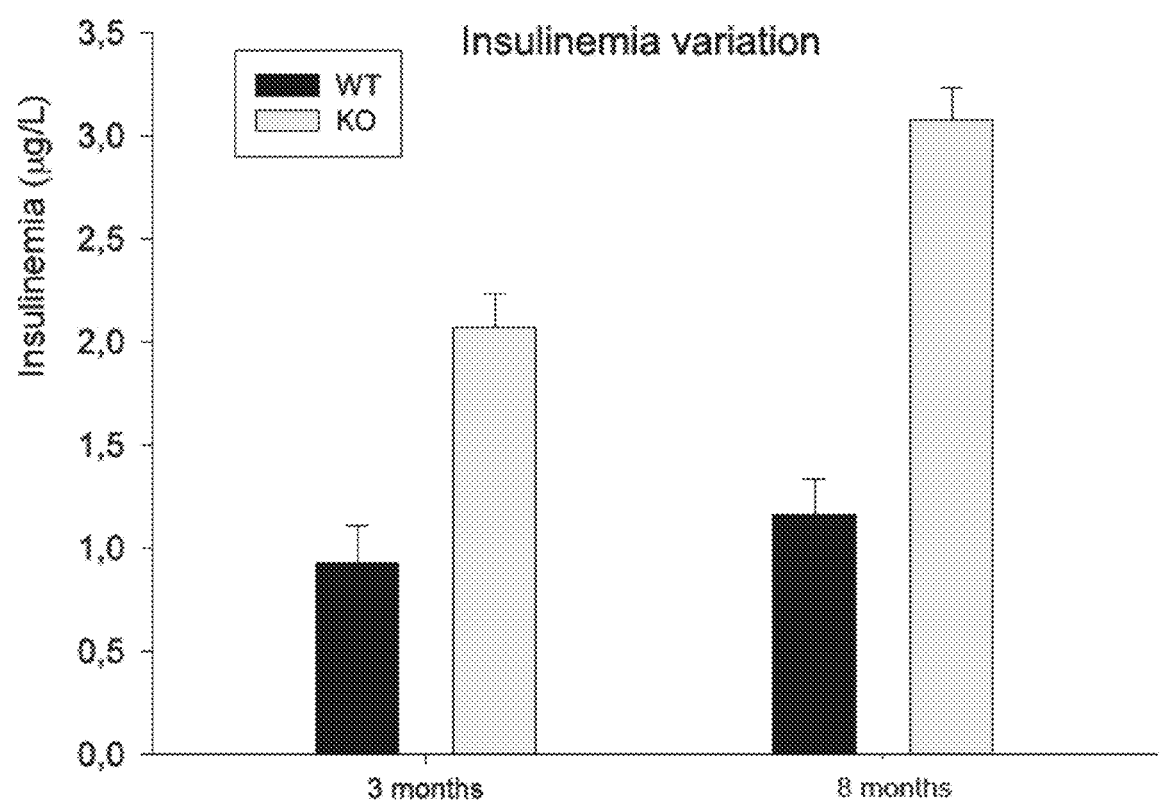
FIG. 4. Insulinemia in 8 wt (black bars) and 8 Maf1 KNO (grey bars) male mice at 3 and 8 months of age as indicated.
Figure 5:
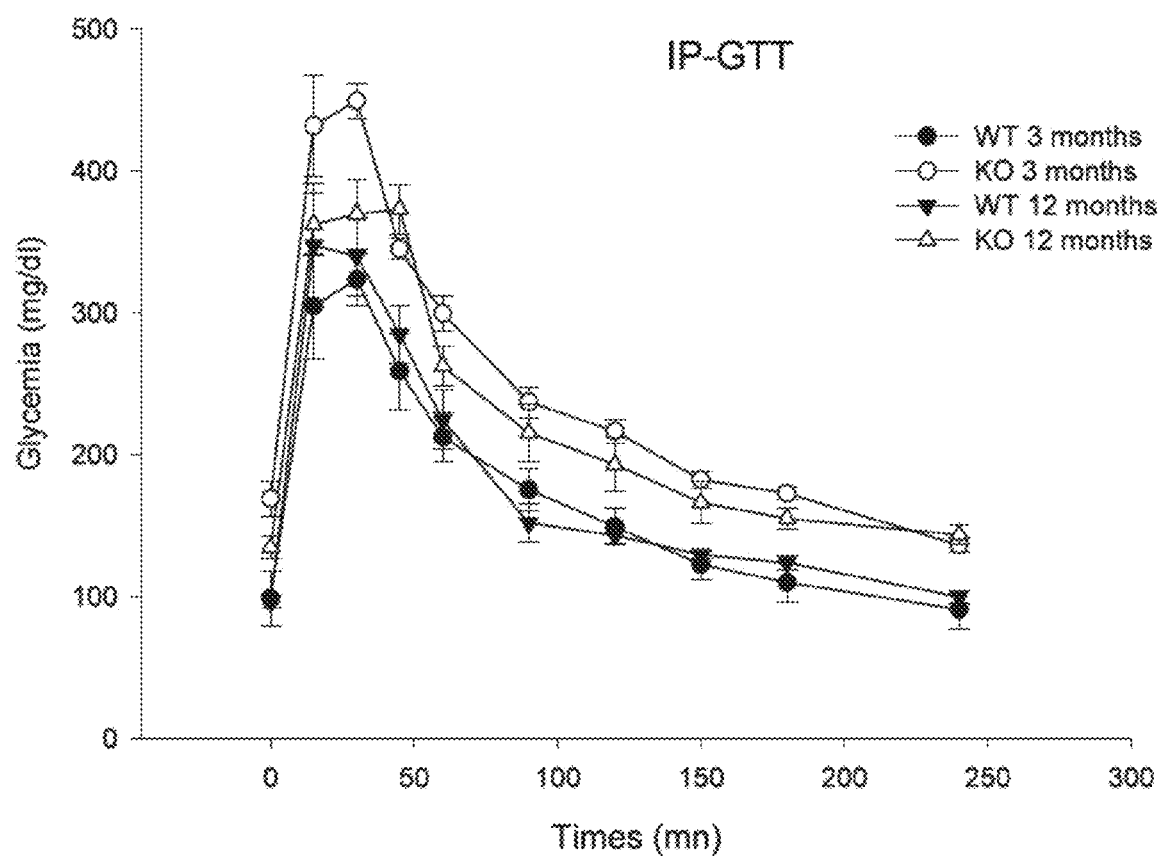
FIG. 5. Intra-peritoneal glucose tolerance test performed with 7 wt (black circles) and 4 Maf1 KO (white circles) 3 month old male mice and 6 wt (white triangles) and 6 Maf1 KO (black triangles) 12 month old mice.

The mice were tested for plasma glucose levels both in a fed state and after an overnight fasting period. In the fed state, plasma glucose levels were the same in wild type and Maf1 KO animals. After a long (16 h) fasting period, however, the Maf1 KO mice were hyperglycemic, with about 130 mg/dl of plasma glucose compared to 90-100 mg/dl of plasma glucose in wild type animals (FIG. 3). The hyperglycemia was similar in young (3 months) and older (11 months) mice. After 16 h of fasting, the mice were also hyperinsulinemic (FIG. 4), and the hyperinsulinemia increased with age. Intra-peritoneal glucose tolerance tests (IP-GTT) conducted after overnight fasting showed that Maf1 KO mice have altered glucose homeostasis based on the increased area under the curves for glucose clearance (FIG. 5). However, the rates of glucose clearance appeared to be comparable between wild type and Maf1 KO mice. To quantify the effect of the Maf1 KO on glucose homeostasis, hyperinsulinemic-euglycemic-clamp tests were performed after a fasting period of 5 h. The rates of glucose disappearance (Rd values) for wild type and Maf1 KO mice are not significantly different. Thus, the hyperglycemia and hyperinsulinemia are observed only after quite extreme fasting conditions (16 h).

Figure 6:
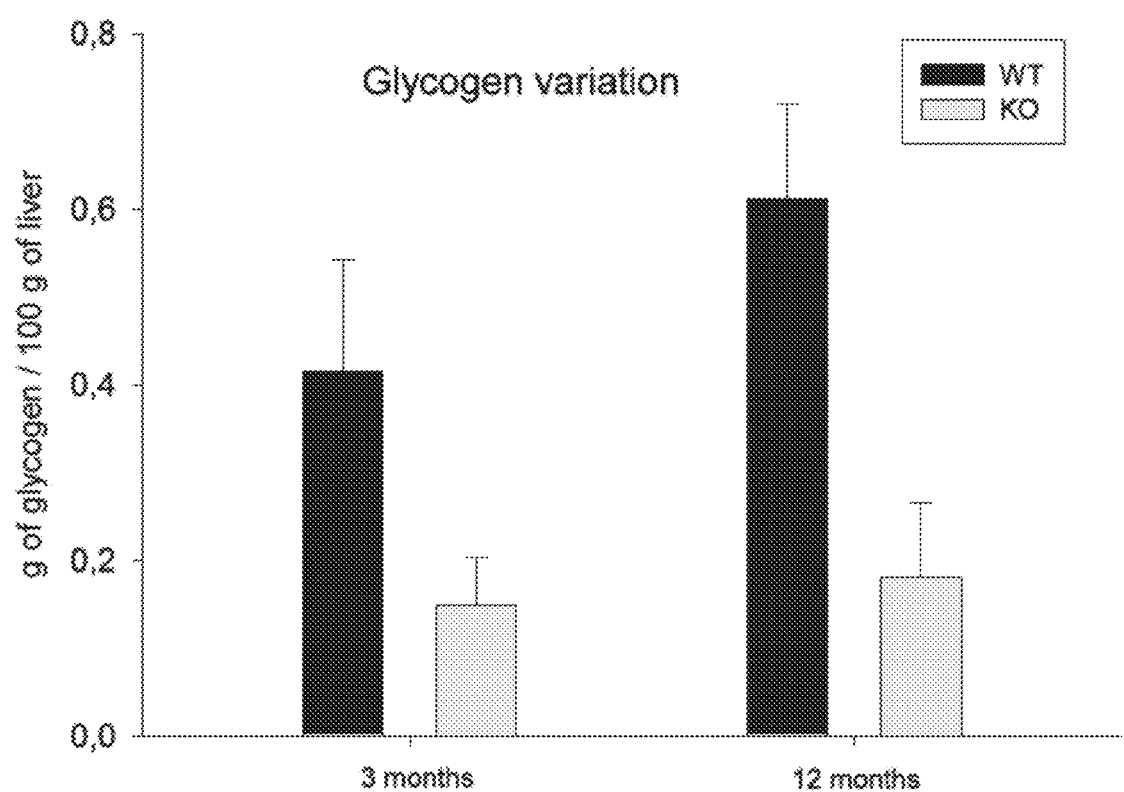
FIG. 6. Glycogen content in 100 g of liver from 8 wt (black bars) and 8 Maf1 KO (grey bars) male mice at 3 or 12 months of age after an overnight period of fasting.

Pancreatic islets appeared morphologically normal in 3 month old mice. Isolated pancreatic islets displayed normal insulin release in response to various glucose concentrations, and pancreatic insulin content was normal. However, after 16 h of fasting, Maf1 KO mice had less glycogen in their livers (less than 0.2 g per 100 g of liver compared to 0.6 g per 100 g of liver in WT mice) (FIG. 6).

Adipose Tissues

Figure 7A:
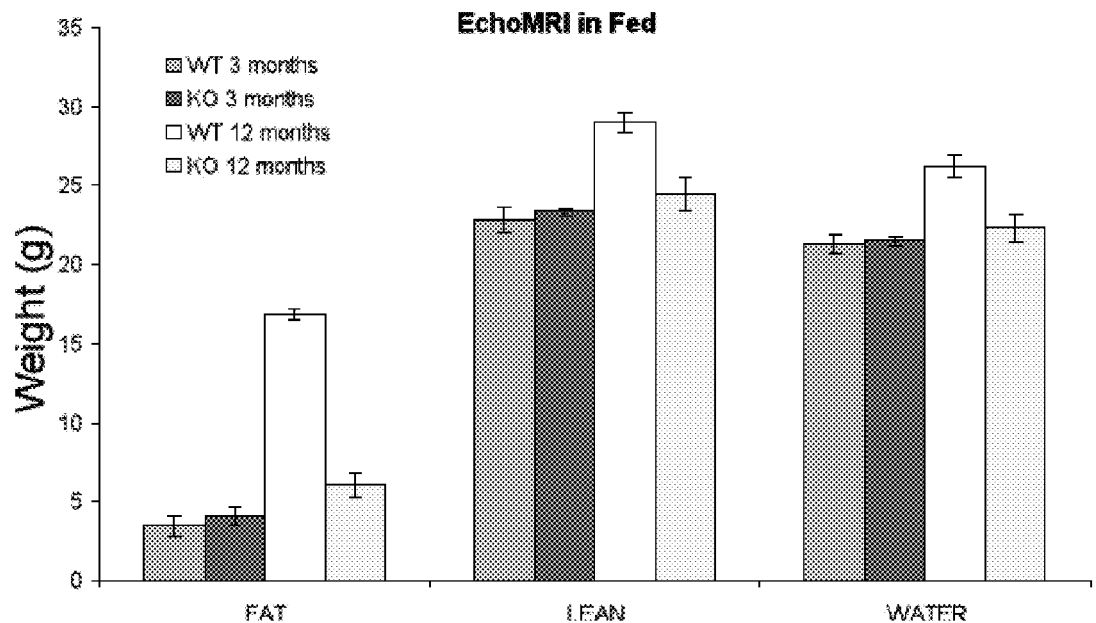
FIG. 7A-7B. EchoMRI performed on 6 wt and 5 Maf1 KO 3 month old male mice as well as 8 wt and 8 Maf1 KO 12 month old mice. (A) Absolute values, (B) ratio relative to body weight.
Figure 7B:
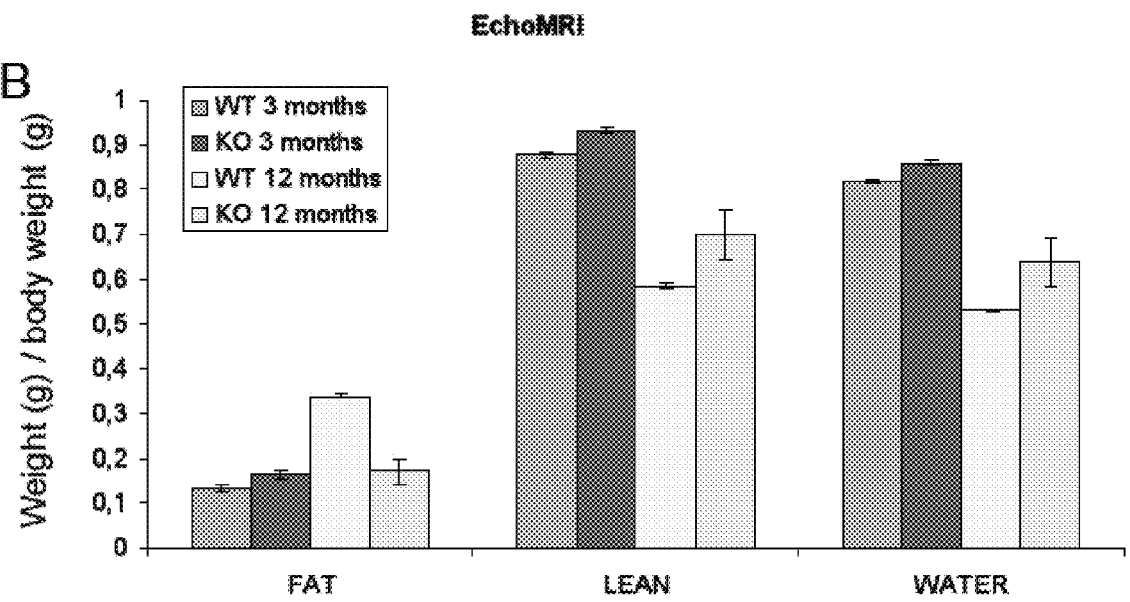

Young Maf1 KO mice (3 month old) were not significantly different from their wild type counterparts in terms of body fat and lean mass content (FIG. 7A). However, older Maf1 KO mice (12 months) were significantly leaner, with an average of only 6 to 7 g of fat versus 16 to 17 g of fat for wild type mice. The total lean mass was also slightly reduced in the knockout consistent with the smaller size of the mice (FIG. 7A). When the same values were expressed as a percentage of the total weight, it was even more evident that the Maf1 KO mice are much leaner (FIG. 7B).

Figure 8A:
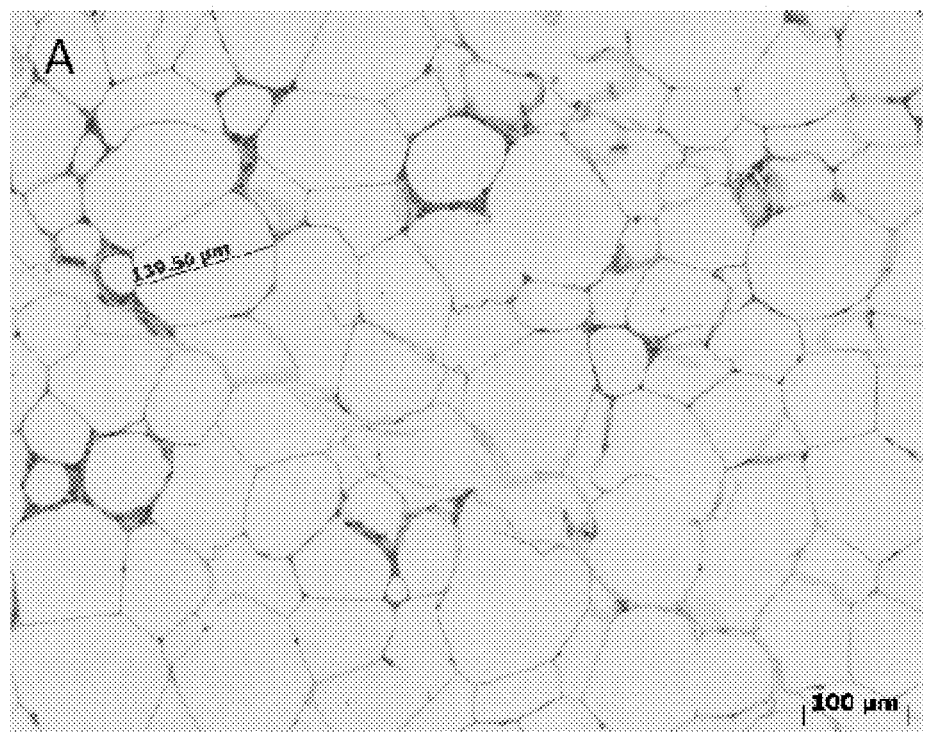
FIG. 8A-8B. Appearance of visceral fat tissue in wt (A) and Maf1 KO (B) male mice of 12 months of age fed a normal diet. The tissues are shown at the same magnification. The cells are much larger in wt mice, with a maximum intracellular cross distance of 139.56 μM and 67.96 μM for the shown wt and Maf1 KO samples, respectively.
Figure 8B:
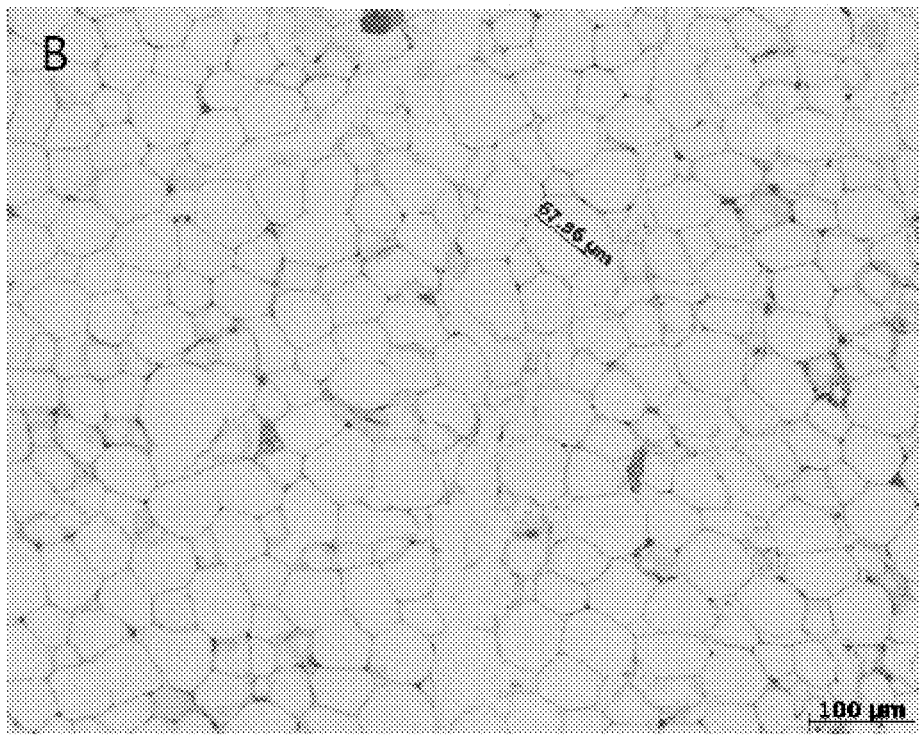

Microscopically, adipocytes derived from visceral fat tissue of wild type mice were much larger than those from Maf1 KO mice (FIG. 8).

Plasmatic Lipid Metabolites

Figure 9:
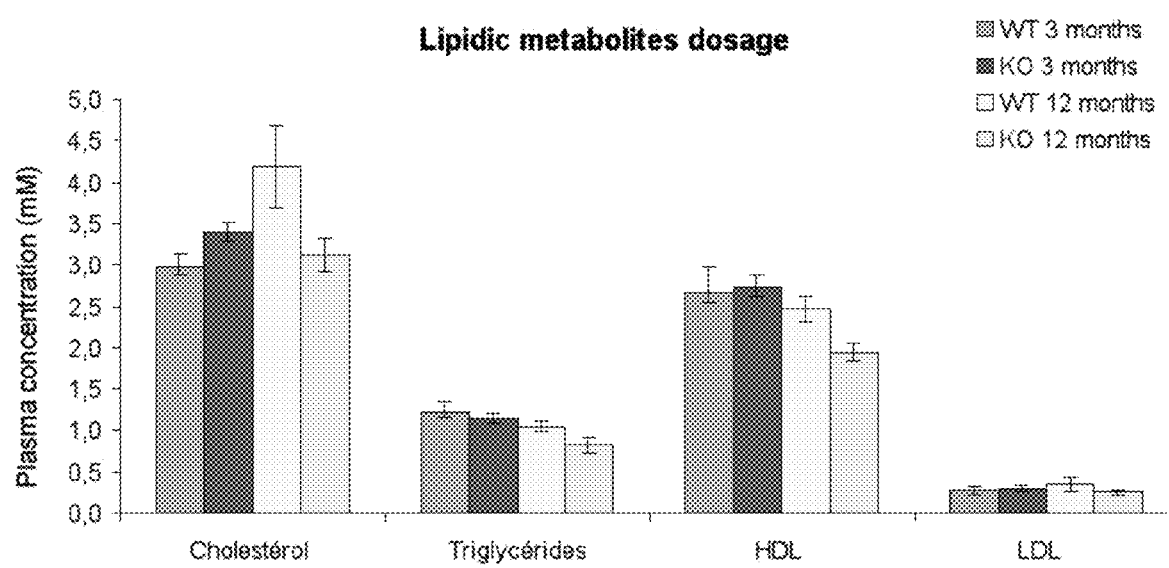
FIG. 9. Dosage of plasmatic lipid metabolites in 8 wt and 8 Maf1 KO mice aged 3 months and 8 wt and 8 Maf1 KO mice aged 12 months.

FIG. 9 shows the concentration of cholesterol, triglycerides, HDL and LDL in the blood. At 12 months of age, Maf1 KO mice had significantly reduced levels of cholesterol and slightly lower levels of triglycerides and HDL. Levels of LDL appeared similar in wild type and Maf1 KO mice.

Effects of High Fat Diet

Figure 10:
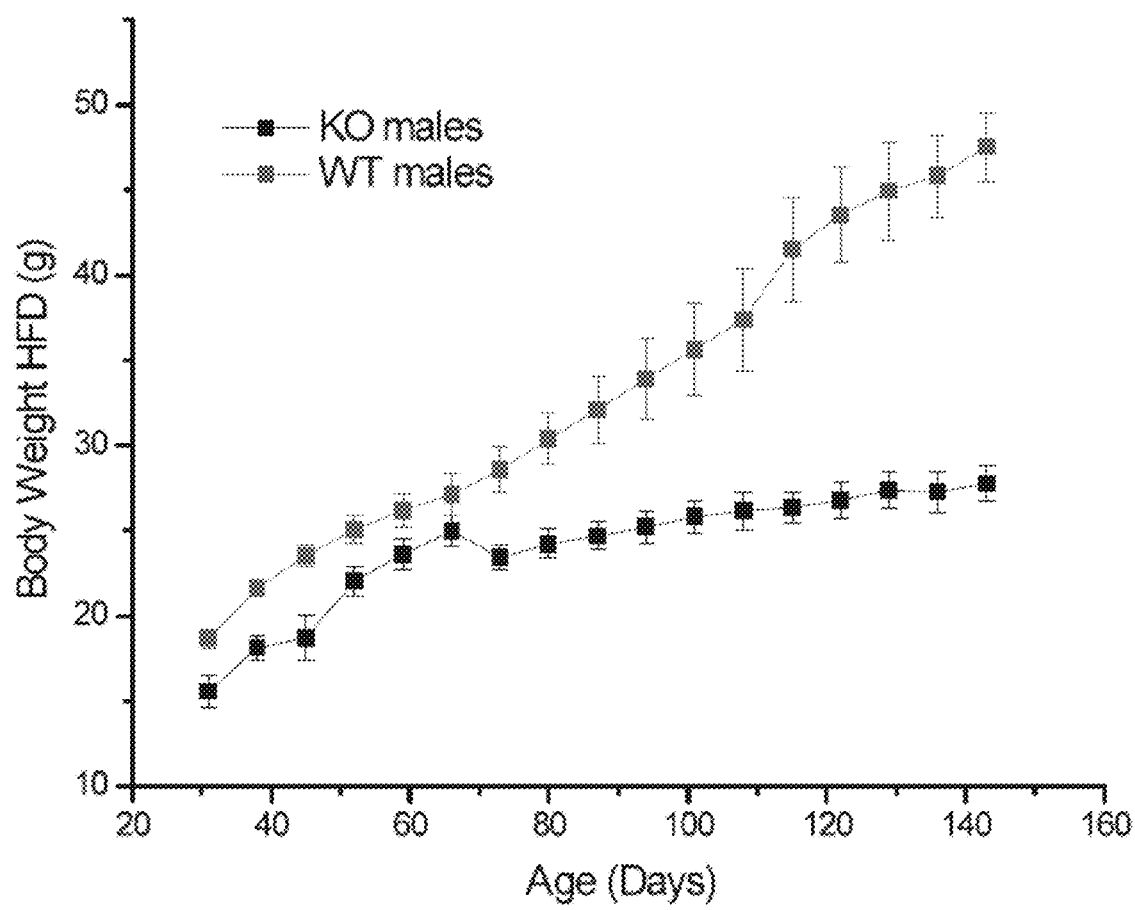
FIG. 10. Body weight of 5 wt (grey squares) and 8 Maf1 KO (black squares) male mice fed a very high fat diet (VHFD, 60% fat) as of 4 weeks of age.
Figure 11:
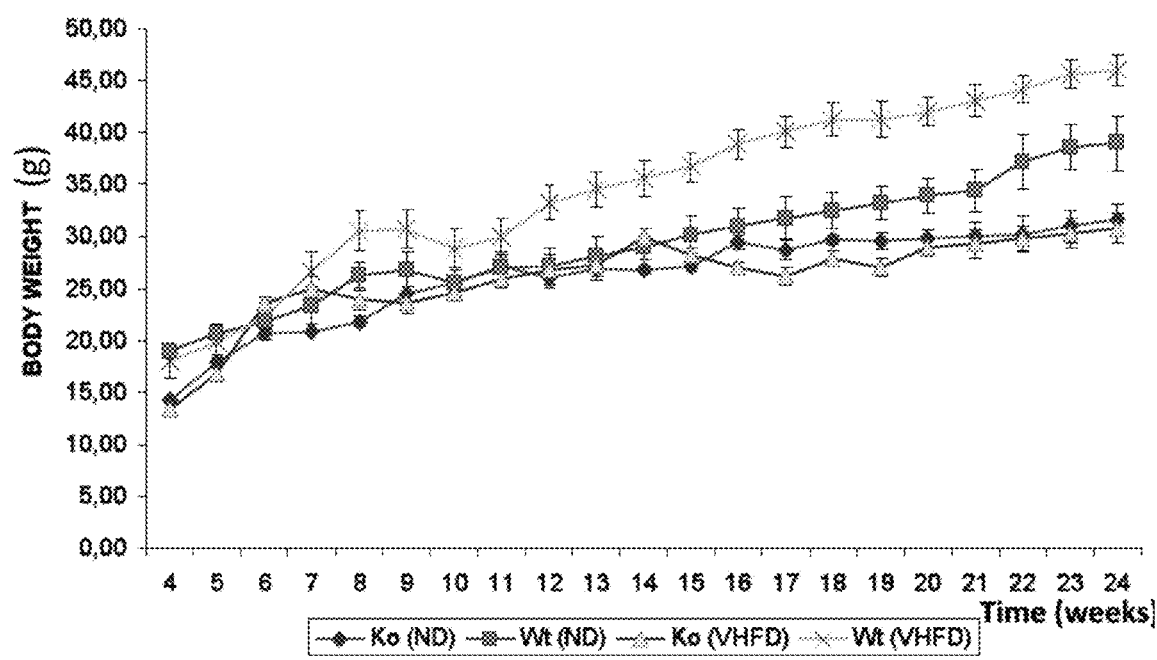
FIG. 11. Body weight of 12 wt and 12 Maf1 KO male mice fed a normal diet (ND, 12% fat) and 12 wt and 12 Maf1 KO male mice fed a very high fat diet (VHFD, 60% fat) as of 4 weeks of age.
Figure 12:
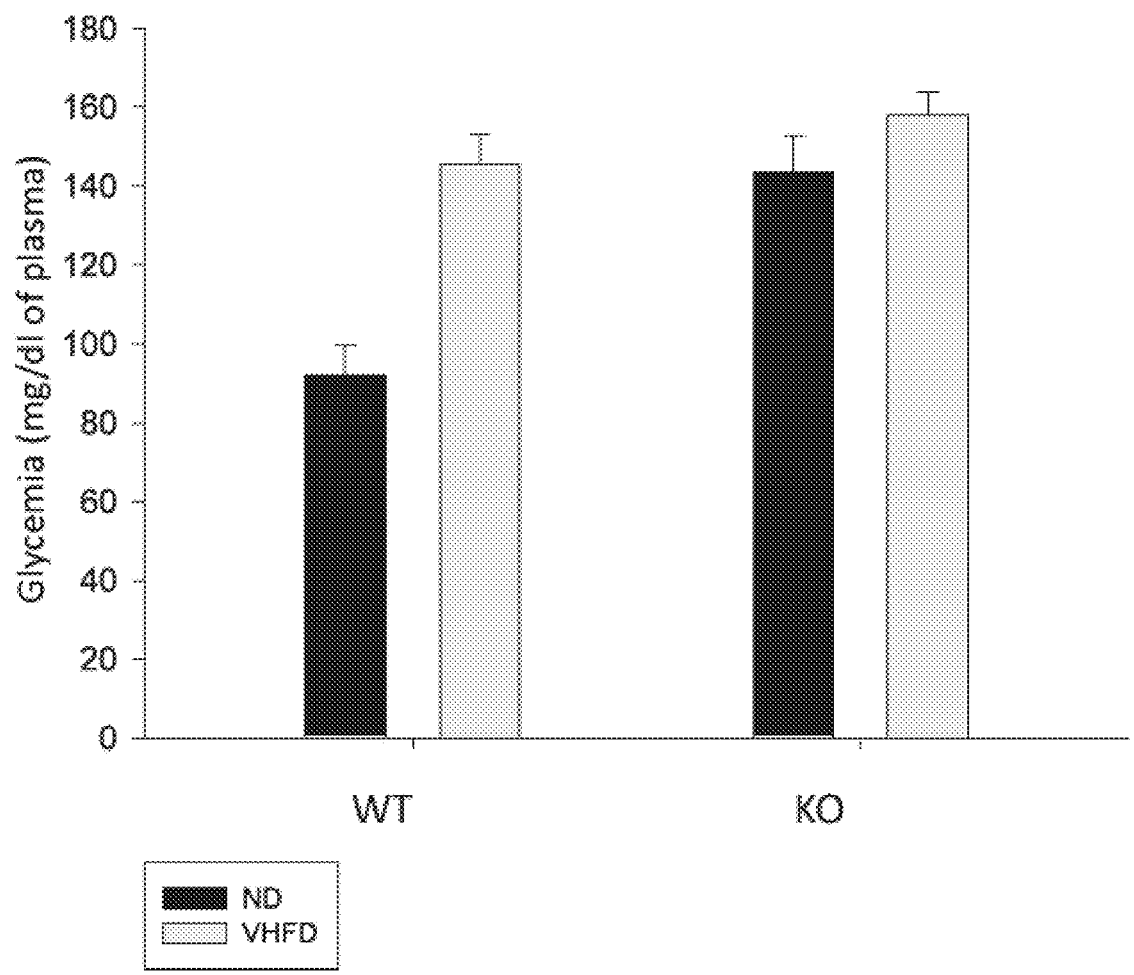
FIG. 12. Glycemia levels in 8 wt and 8 Maf1 KO 3 month old male mice maintained under normal (black bars) or very high fat (grey bars) diet, after 16 h fasting.
Figure 13:
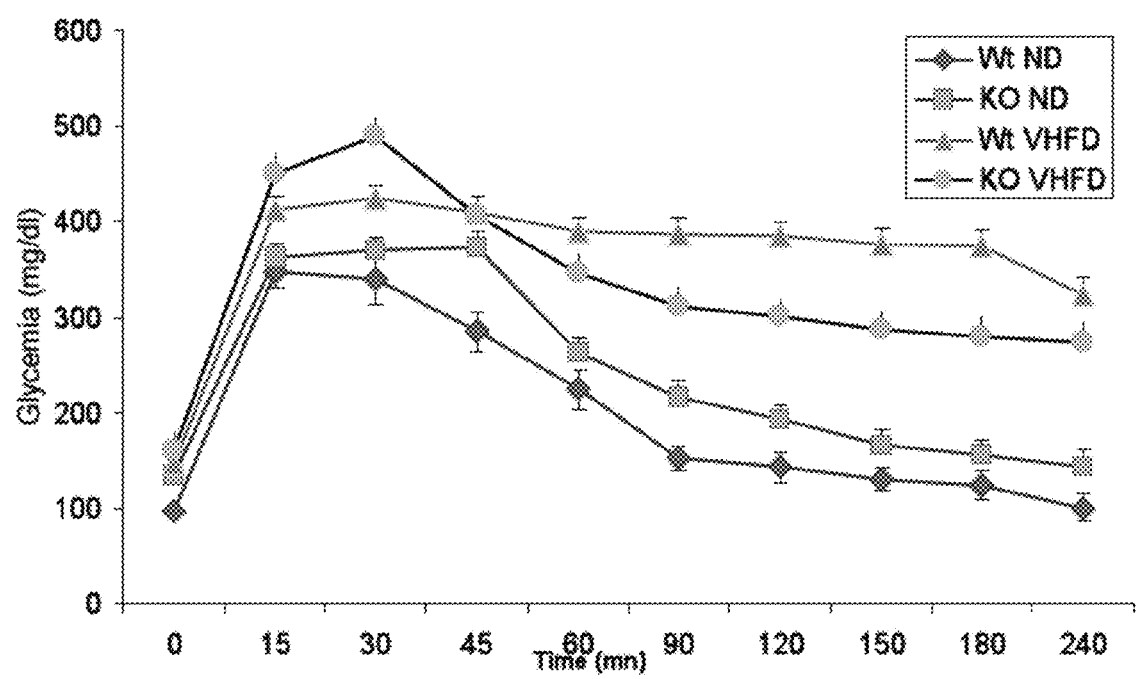
FIG. 13. Intra-peritoneal glucose tolerance test performed with wt (diamonds) (n=12) and Maf1 KO (squares) (n=12) male mice under normal diet or wt (triangles) (n=12) and Maf1 KO (circles) (n=12) male mice under very high fat diet. All mice were 3 months old.

The results above prompted testing as to whether Maf1 KO mice might be resistant to a high fat diet. Wild type and Maf1 KO male mice were subjected to a very high fat diet (60% calories from fat) as of 4 weeks of age. FIG. 10 shows the weight evolution of these mice. Whereas wild type mice displayed a significant increase in weight, reaching more than 45 g after 20 weeks, the Maf1 KO mice averaged 27-28 g at the same age. FIG. 11 shows a similar experiment with a second mouse cohort, comparing wild type and Maf1 KO mice on either normal or very high fat diets. Whereas wild type animals gain substantially more weight on a high fat diet than on a normal diet, Maf1 KO animals are resistant to this weight gain and have the same body weight whether on a normal or high fat diet. Similarly, whereas wild type mice had a clear increase in glycemia after overnight fasting, from about 90-100 mg/dl to 140-150 mg/dl, the Maf1 KO mice varied little from their starting value of about 130-140 mg/dl (FIG. 12). Thus, Maf1 KO mice are more resistant than wild type mice to an increase in glycemia from their starting level. The better resistance of the Maf1 KO mice was also apparent during an IP-GTT test (FIG. 13), where Maf1 KO mice on a very high fat diet reduced their plasma glucose concentration more efficiently than wild type mice.

Figure 14A:
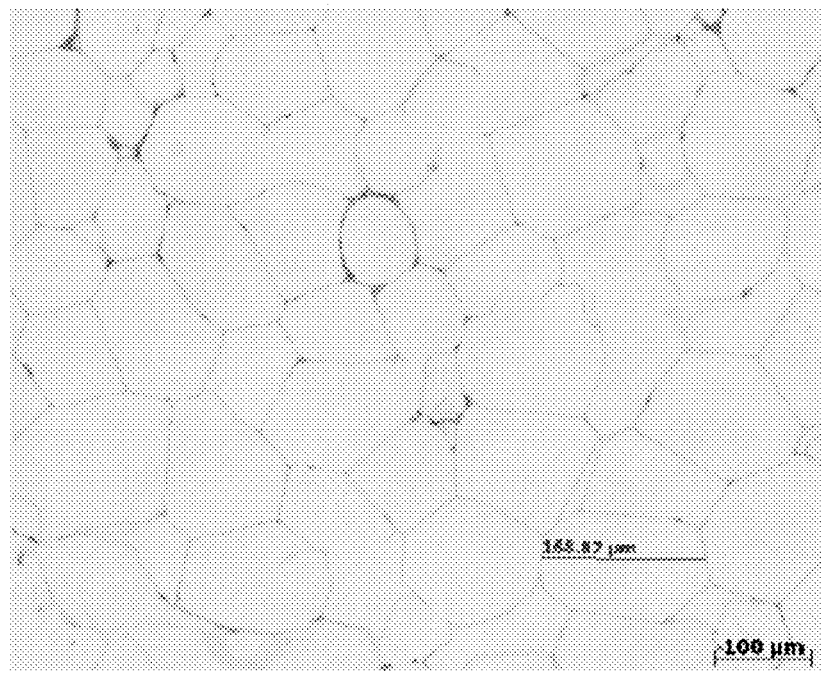
FIG. 14A-14B. Appearance of visceral fat tissue in wt (A) and Maf1 KO (B) male mice of 24 weeks of age fed a very high fat diet from week 4. The tissues are shown at the same magnification. The cells are on average larger in the wt mouse, with a maximum intracellular cross distance of 168.87 μM and 120.45 μM for the shown wt and Maf1 KO samples, respectively.
Figure 14B:
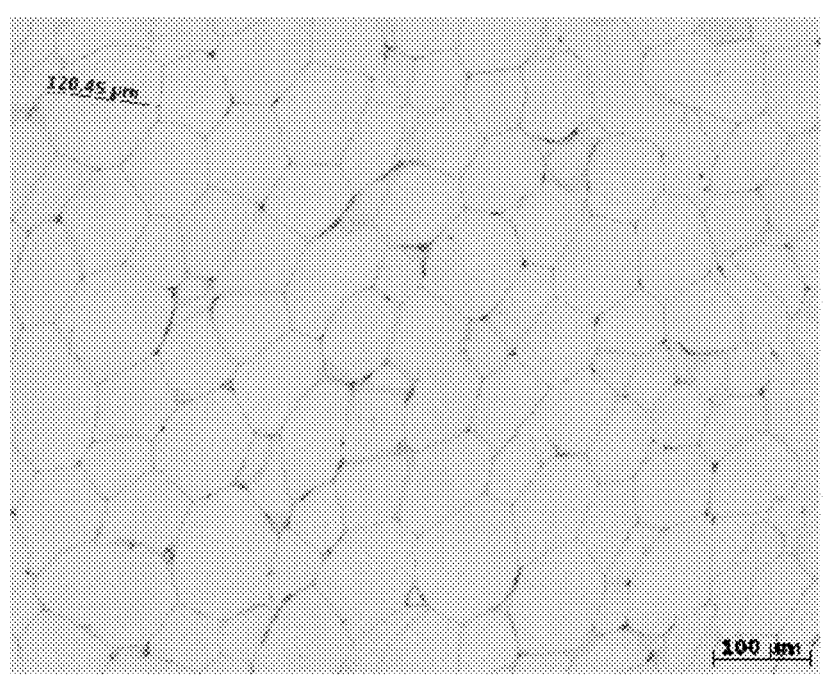

Microscopic examination of adipocytes from visceral fat tissues revealed an increase in the size of adipocytes in both wild type and Maf1 KO mice. Although the percent increase was smaller for wild type animals than for Maf1 KO animals (121% versus 177%), the final adipocyte size was larger for wild type animals (maximal intracellular cross distance of 168.86 µM versus 120.45 for Maf1 KO adipocytes (FIG. 14)).

Figures 15A, 15B:
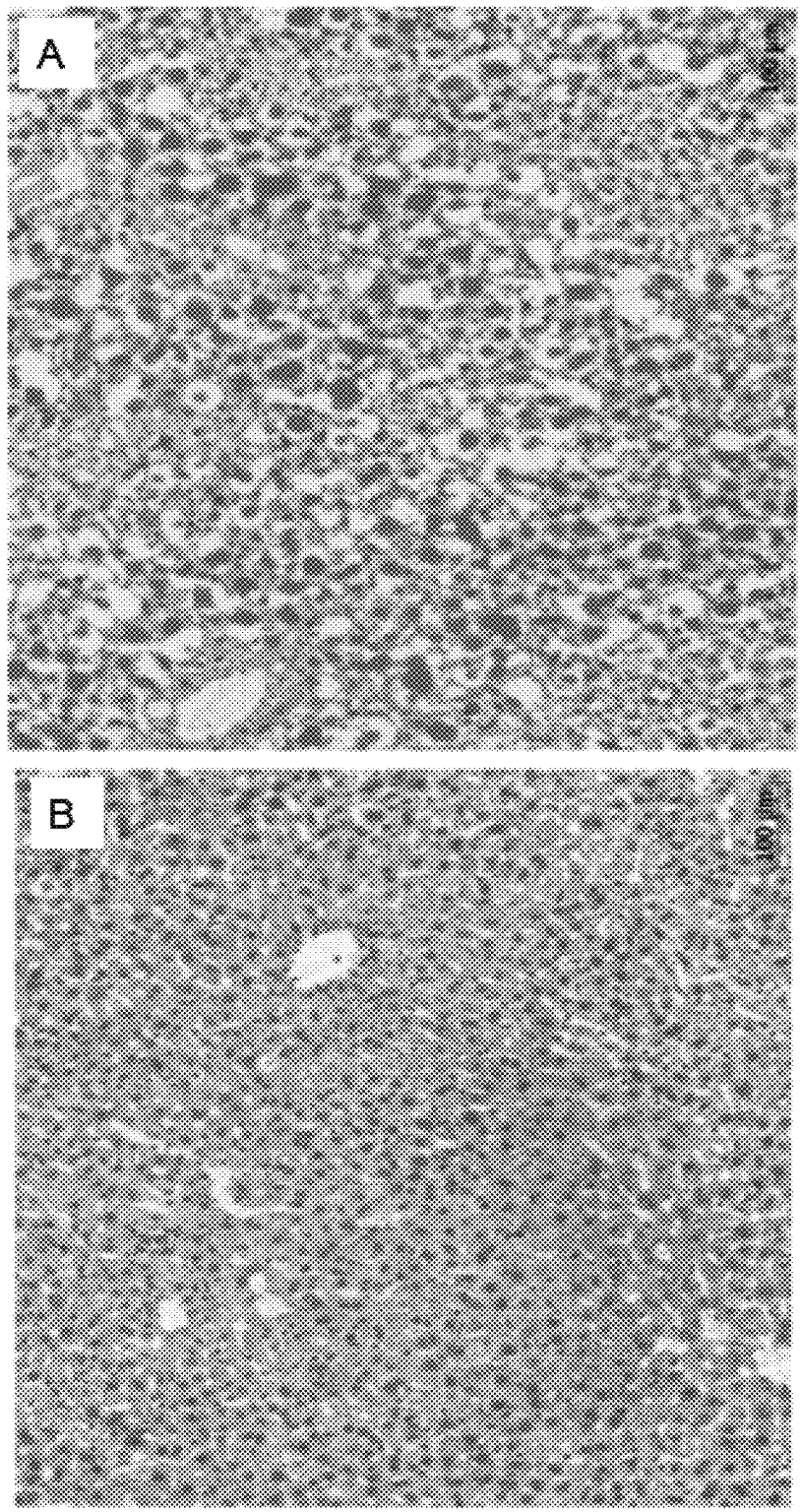
FIG. 15A-15B. Liver sections from 12 month old wt (A) and Maf1 KO (B) male mice fed a normal diet. The tissues are shown at the same magnification. The sections were stained with oil red.
Figures 16A, 16B:
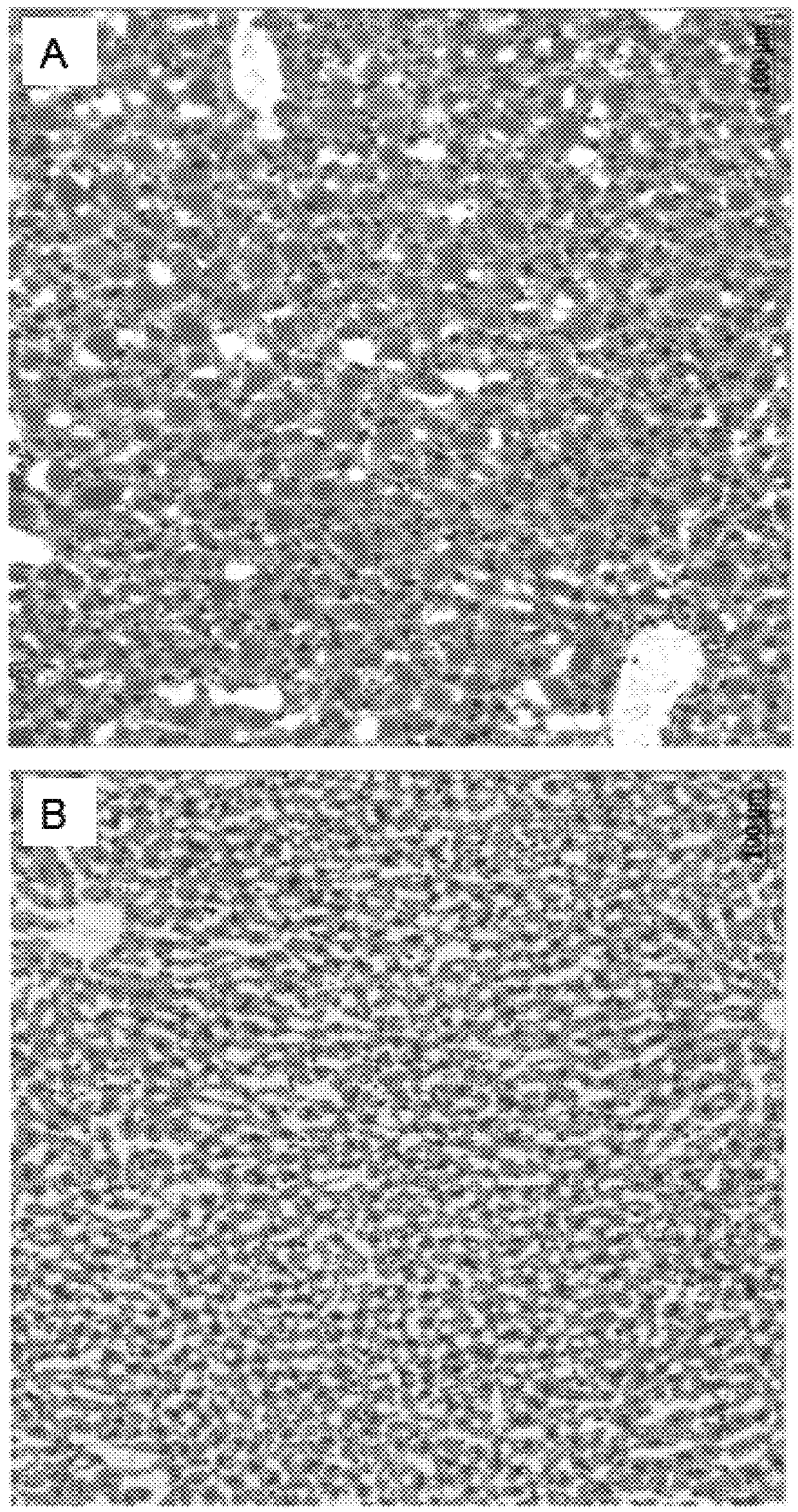
FIG. 16A-16B. Liver sections from 24 week old wt (A) and Maf1 KO (B) male mice, fed a very high diet as of week 4. The tissues are shown at the same magnification. The sections were stained with oil red.

Histological examination of liver sections of mice fed a normal diet revealed hepatocytes with much more lipid in wild type mice as compared to Maf1 KO mice (FIG. 15). After 24 weeks on a very high fat diet, the hepatocytes of wild type mice were engorged with lipid, whereas Maf1 KO mice showed nearly no lipid accumulation (FIG. 16). Thus, the Maf1 KO mice appear highly resistant to diet-induced obesity and fat accumulation in the liver.

Gene Expression Arrays in Wild Type and Maf1 KO Mice Under Fasting Conditions

To investigate the global change in gene expression resulting from the lack of the Maf1 gene, mRNA levels were measured with Nimblegen expression arrays in visceral adipose tissues from wild type and Maf1 KO mice at 18 weeks of age, after an overnight period of fasting. Mice aged 18 weeks were chosen because at that age, they still have a fat mass similar to that of wild type animals (FIG. 7). The results indicated 408 downregulated and 303 upregulated probes with an adjusted P value smaller than 0.05, corresponding to 316 downregulated and 259 upregulated genes. A functional enrichment analysis of these data (with FatiGO), showed a highly significant enrichment of down-regulated genes for GO terms associated with lipid metabolism as well as related processes such as sterol and steroid metabolism (Table 2).

TABLE 2

Functional enrichment analysis of genes down-regulated in visceral adipose tissue of Maf1 KO mice.

| Index | Term | Adjusted p value |
|---|---|---|
| | GO biological process at level 4 | |
| 0 | lipid matabolic process (GO:0006629) | 3.09e−6 |
| 0 | alcohol metabolic process (GO:006066) | 4.11e−6 |
| 0 | response to pheromone (GO:0019236) | 6.69e−4 |
| 0 | hormone metabolic process (GO:0042445) | 6.69e−4 |
| 0 | generation of precursor metabolites and energy (GO:0006091) | 2.55e−3 |
| 0 | vitamin metabolic process (GO:0006766) | 7.87e−3 |
| | GO biological process at level 5 | |
| 1 | cellular lipid metabolic process (GO:0044255) | 9.34e−8 |
| 1 | electron transport (GO:0006118) | 1.5e−4 |
| 1 | fat-soluble vitamin metabolic process (GO:0006775) | 1.54e−2 |
| | GO biological process at level 6 | |
| 2 | steroid metabolic process. (GO:0008202) | 1.3e−13 |
| 2 | lipid biosynthetic process (GO:0008610) | 1.39e−8 |
| 2 | isoprenoid metabolic process (GO:0006720) | 2.2e−5 |
| | GO biological process at level 7 | |
| 3 | steroid biosynthetic process (GO:0006694) | 5.69e−13 |
| 3 | sterol metabolic process (GO:0016125) | 6.42e−12 |
| 3 | isoprenoid biosynihiatsc process (GO:0008299) | 2.71e−3 |
| | GO biological process at level 8 | |
| 4 | sterol biosynthetic process (GO:0016126) | 1.21e−12 |
| 4 | cholesterol metabolic process (GO:0008203) | 8.59e−9 |
| | GO biological process at level 9 | |
| 5 | cholesterol biosynthetic process (GO:0006695) | 4.71e−9 |

FatiGO analysis was used to compare GO bioprocess terms enriched among 306 genes whose expression decreased in adipose tissue of 18 week old Maf1 KO mice versus wild type. Significance was calculated by comparing the frequencies of the same GO terms among the 24375 genes present on the microarray. The enrichment of all of the indicated GO terms was highly significant.

The array analysis revealed that in addition to the lack of Maf1 expression, the genetic deletion also caused overexpression of a neighbouring gene coding for the protein KIAA1875. The phenotypes observed with the Maf1 KO mice may thus be caused by the lack of Maf1, the overexpression of KIAA1875, or a combination of both.

To further investigate the basis of the obesity and lipotoxicity resistance of Maf1 KO mice, food intake and energy expenditure was monitored in Oxymax calorimetry cages. Studies of food intake conducted with age-matched (16 week old) or weight-matched male mice revealed a reproducible and statistically significant reduction in food consumption in the knockout (e.g., FIG. 17). These experiments identify a behavioural phenotype of the Maf1 KO, reduced feeding, which contributes to the lower body weight of the animals.

Food intake-growth rate correlations (see The Mouse Phenome Database) indicate that the reduced food consumption of Maf1 KO mice is not sufficient to account for the difference in body weight relative to wild-type animals. Since intestinal absorption of dietary fat was equivalent between wild-type and Maf1 KO mice (data not shown), it was deduced that a combination of behavioural and metabolic phenotypes contribute to the leanness and obesity-resistance of the Maf1 KO.

Figure 17:
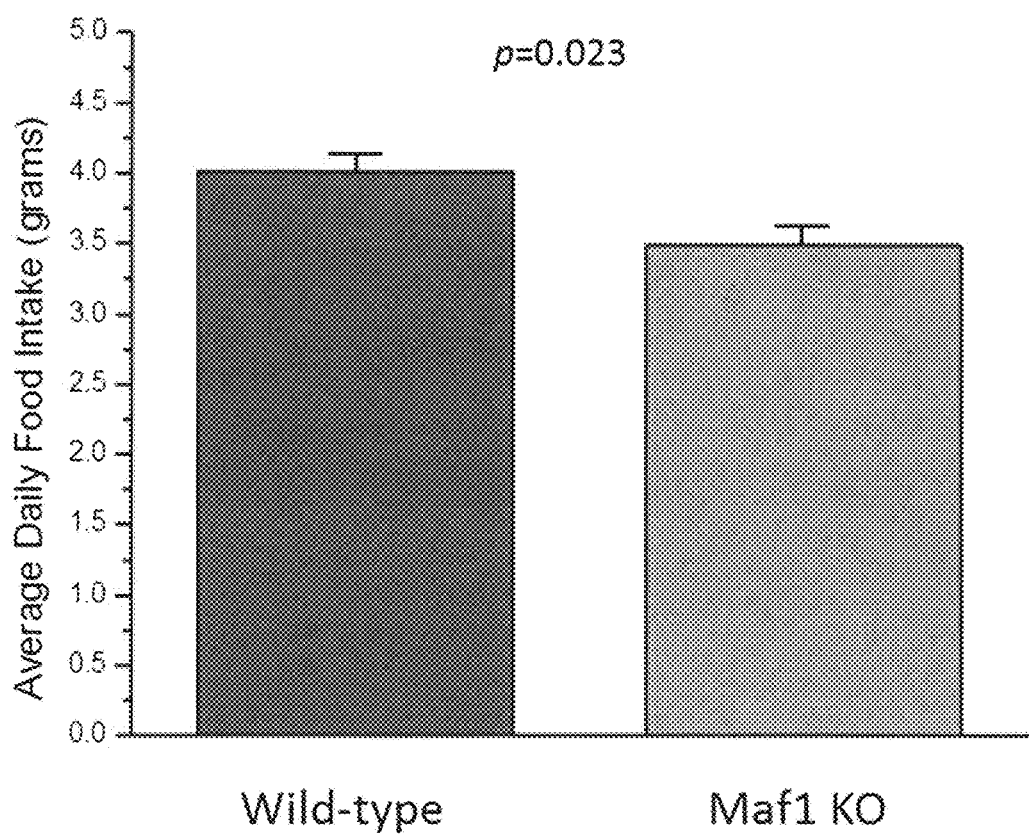
FIG. 17. Average daily food intake of wild-type and Maf1 KO mice. Data were collected during indirect calorimetry measurements in metabolic cages (Columbus Instruments) over 3 days. Animals were weight-matched (WT 25.1±1.5 g, n=3 and KO 25.5±0.7 n=4, body weight±standard deviation) and fed a regular chow diet. Statistical significance was calculated using a Student's unpaired t-Test and has been achieved (p<0.05) in three independent experiments.
Figure 18:
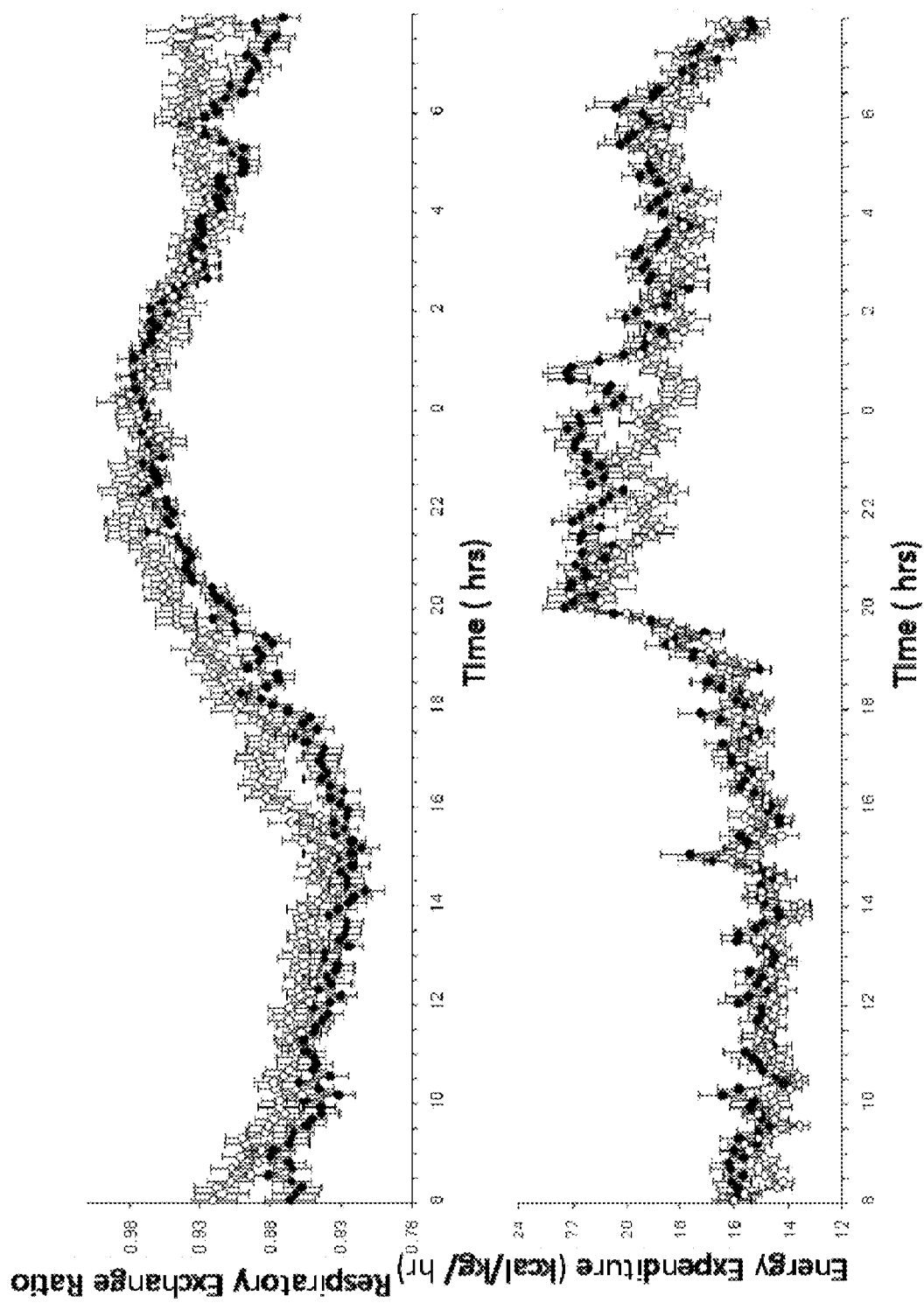
FIG. 18. Indirect calorimetry of wild-type and Maf1 KO mice. Data were collected using an Oxymax indirect calorimetry system. Four male mice of each genotype (16 weeks of age) maintained on a regular chow diet were monitored for 1 week following a 48 hour acclamation period. Average data for the 7 days are plotted for WT (open circles) and KO (closed circles) animals at each time point to demonstrate the diurnal cycle. Simultaneous measurement of locomotor activity showed no difference.

Changes in lipid metabolism in the knockout are evident from the aforementioned gene expression profiling of adipose tissue (Table 2) as well as from the levels of plasma lipid metabolites (FIG. 9). Consistent with these data, measurements of oxygen consumption and carbon dioxide production showed that Maf1 KO mice preferentially utilize fatty acids over carbohydrates as metabolic fuel during the daylight and evening hours (lower respiratory exchange ratio (RER), FIG. 18), periods when their food consumption and activity level is low and begins to increase. Energy expenditure during the same period was indistinguishable but diverged thereafter with the knockout animals producing more energy as heat during active feeding even though they consume less food (FIGS. 17 and 18). Locomotor activity of the animals was indistinguishable.

Figure 19:
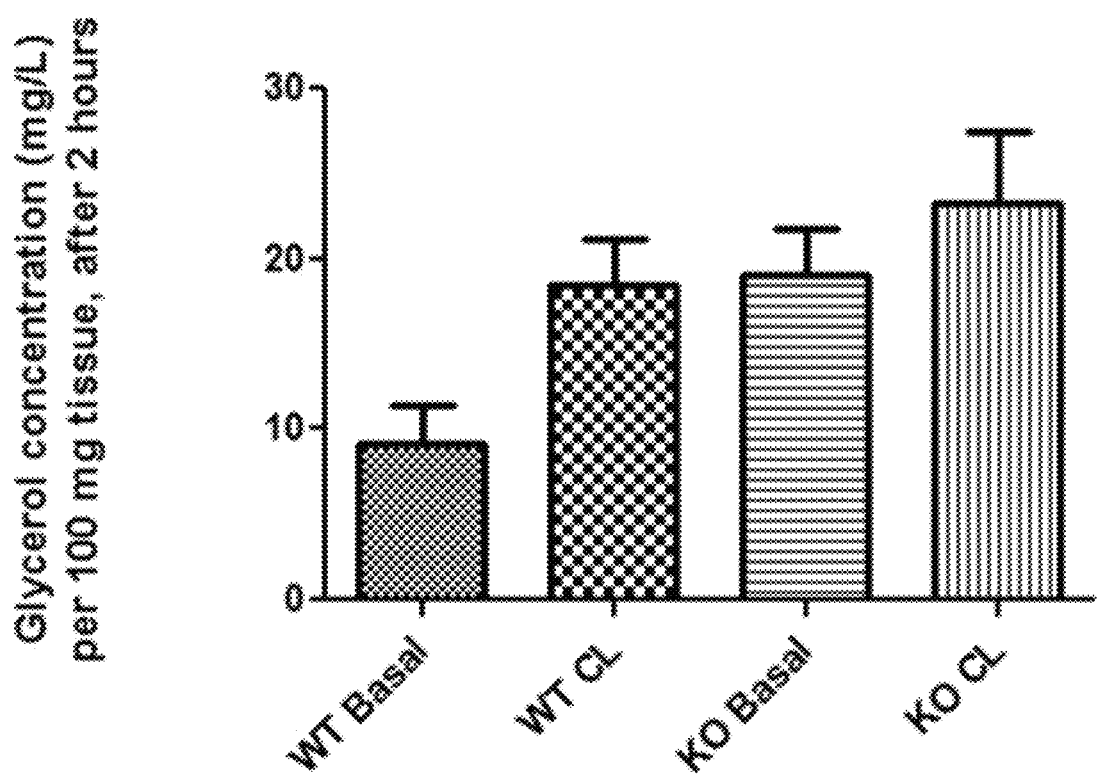
FIG. 19. Lipolysis assay in adipose tissue explants of wild-type and Maf1 KO mice. Glycerol production in visceral adipose tissue explants was measured over 90 minutes in buffer with or without the beta3 adrenergic receptor agonist CL-316,243. Data were normalized for adipose tissue mass. Animals were twelve months old and were maintained on a regular chow diet. Glycerol concentrations represent the average±standard deviation of 4 animals of each genotype.

The lean phenotype and increased energy expenditure of Maf1 KO mice suggested that lipolysis might be elevated in order to provide an increased supply of fatty acids for β-oxidation. Measurements of the rate of glycerol production in visceral adipose tissue explants confirmed a two-fold increase in lipolysis in the knockout versus wild-type tissue (FIG. 19). The increase in lipolysis in Maf1 KO tissue was epistatic to treatment with the β3-adrenergic agonist CL-316243 in contrast to wild-type tissue which showed the expected increase in lipolysis in response to the agonist.

Figure 20:
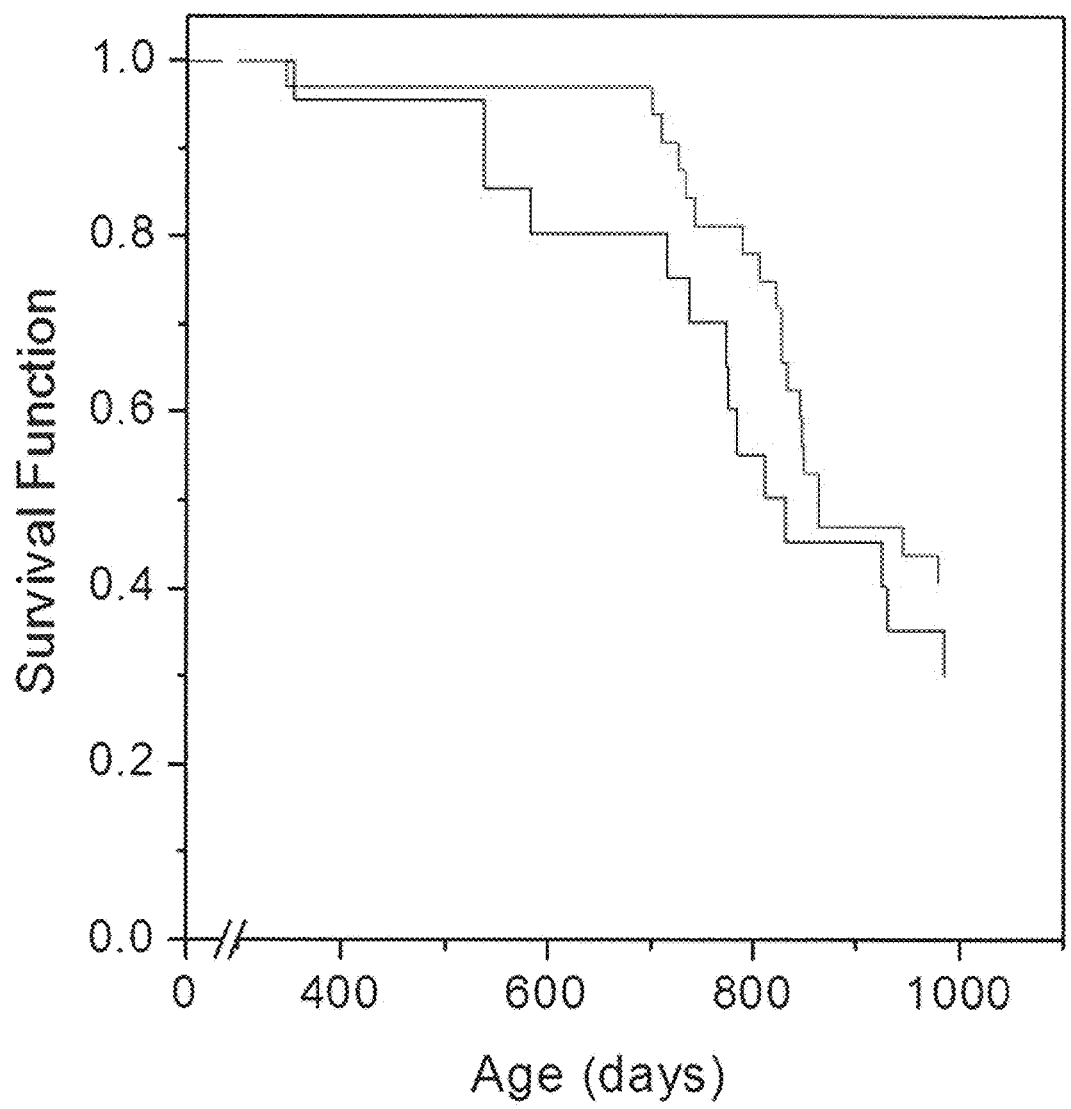
FIG. 20. Lifespan of wild-type and Maf1 KO mice. Kaplan-Meier survival curves for male WT (curve on lower left) and Maf1 KO (curve on upper right) mice. At this stage of the experiment, the average lifespan (±SEM) is estimated to be 811±41 days (n=20) and 869±24 days (n=32) for wild-type and KO animals, respectively. The lifespan of the animals is not statistical different. Surviving animals are >900 days old.

To obtain an overall assessment of the potential long term benefits or consequences of a whole body Maf1 knockout in the mouse, a longevity study of the animals was conducted. At the present time (2011), more than 60% of the animals of both genotypes have died. Kaplan-Meier estimates of the mean lifespan of the knockout relative to the parental C57BL/6J strain indicate that there is no statistically significant difference between the two strains on a regular chow diet (FIG. 20). Thus, pharmacological treatments that achieve obesity resistance in a mechanistically similar manner to the Maf1 KO are likely to be well tolerated.

3. Discussion

Envisioned Medical Applications

The characterization of the Maf1 KO mice indicates that the deletion in the Maf1 KO mice identifies targets to develop drugs aimed at controlling hypercholesterolemia as well as weight problems including diet-induced obesity and associated diseases (cardiovascular disease and non-alcoholic fatty liver disease). Given that the deletion removes the Maf1 gene, it is highly likely that the lean phenotype results from the absence of Maf1. It could also, however, result from other effects of the genetic deletion such as overexpression of KIAA1875.

What is claimed is:

1. A method for determining a putative agent that treats obesity and/or an obesity related disease, the method comprising contacting cells having Maf1 with the putative agent and measuring the activity and/or level of Maf1, wherein the cells are adipocytes, liver cells, or visceral fat tissue, wherein inhibition or downregulation of Maf1 in the presence of the putative agent indicates that the putative agent is a candidate for treating obesity and/or an obesity related disease, and wherein a lack of inhibition or downregulation of Maf1 in the presence of the putative agent is indicative that the putative agent is not a candidate for treating obesity and/or an obesity related disease.

2. The method of claim 1, wherein the cells are located in vivo.

3. The method of claim 1, wherein the cells are located in vitro.

4. The method of claim 1, wherein measuring the activity and/or level of Maf1 comprises detecting Maf1 protein or mRNA levels.

5. The method of claim 4, wherein detecting Maf1 protein or mRNA levels comprises immunoblotting, biochemical assay, or RNA analysis.

6. The method of claim 1, wherein measuring the activity and/or level of Maf1 comprises measuring cell weight, cell size, cellular lipid levels, cellular glucose clearance, or plasma lipid or cholesterol levels.

7. The method of claim 1, the method comprising maintaining the cells under conditions which (1) result in increased cell weight, increased cell size, cellular lipid buildup, impaired cellular glucose clearance, or increased plasma lipid or cholesterol levels in the absence of a putative agent that inhibits or downregulates Maf1 and (2) do not result in increased cell weight, increased cell size, cellular lipid buildup, impaired cellular glucose clearance, or increased plasma lipid or cholesterol levels in the presence of a putative agent that inhibits or downregulates Maf1, wherein a lack of increased cell weight, increased cell size, cellular lipid buildup, impaired cellular glucose clearance, or increased plasma lipid or cholesterol levels is indicative that the putative agent is a candidate for treating obesity and/or an obesity related disease and wherein increased cell weight, increased cell size, cellular lipid buildup, impaired cellular glucose clearance, increased plasma lipid or cholesterol levels is indicative that the putative agent is not a candidate for treating obesity and/or an obesity related disease.

8. The method of claim 7, wherein the cells are maintained under the conditions between 3 hours and 12 months.

9. The method of claim 7 comprising a control comprising measuring cell weight, cell size, cellular lipid levels, cellular glucose clearance, or plasma lipid or cholesterol levels of Maf1 knockout cells, wherein a lack of increased cell weight, increased cell size, cellular lipid buildup, impaired cellular glucose clearance, or increased plasma lipid or cholesterol levels of the cells contacted with the putative agent relative to the control is indicative that the putative agent is a candidate for treating obesity and/or an obesity related disease and wherein increased cell weight, increased cell size, cellular lipid buildup, impaired cellular glucose clearance, or increased plasma lipid or cholesterol levels of the cells contacted with the putative agent relative to the control is indicative that the putative agent is not a candidate for treating obesity and/or an obesity related disease.

10. The method of claim 7 comprising a control comprising measuring weight, cell size, lipid levels, glucose clearance of cells, or plasma lipid or cholesterol levels in the absence of the putative agent, wherein increased cell weight, increased cell size, cellular lipid buildup, impaired cellular glucose clearance, or increased plasma lipid or cholesterol levels of the control relative to the cells contacted with the putative agent is indicative that the putative agent is a candidate for treating obesity and/or an obesity related disease and wherein a lack of increased cell weight, increased cell size, cellular lipid buildup, impaired cellular glucose clearance, or increased plasma lipid or cholesterol levels relative to the cells contacted with the putative agent is indicative that the putative agent is not a candidate for treating obesity and/or an obesity related disease.

11. The method of claim 1, wherein the conditions comprise a high-fat diet.

12. The method of claim 1, wherein the conditions comprise a lipid rich medium.

13. The method of claim 1, wherein the cells are mammalian.

14. The method of claim 13, wherein the cells are human.

15. The method of claim 1, wherein the putative agent inhibits or downregulates Maf1.

16. The method of claim 1, wherein the putative agent is an aptamer, siRNA, antibody, antibody fragment, protein, protein fragment, chemical, small compound or polypeptide.

17. The method of claim 1, wherein the obesity related disease is selected from the group consisting of metabolic syndrome, insulin resistance, type 2 diabetes, dyslipidemia, cardiovascular disease, and non-alcoholic fatty liver disease.

* * * * *

SEQUENCE LISTING

<160> NUMBER OF SEQ ID NOS: 2

<210> SEQ ID NO 1
<211> LENGTH: 256
<212> TYPE: PRT
<213> ORGANISM: Homo sapiens -continued

<400> SEQUENCE: 1

| Met | Lys | Leu | Leu | Glu | Asn | Ser | Ser | Phe | Glu | Ala | Ile | Asn | Ser | Gln | Leu |
|---|---|---|---|---|---|---|---|---|---|---|---|---|---|---|---|
| 1 | | | | 5 | | | | | 10 | | | | | 15 | |

| Thr | Val | Glu | Thr | Gly | Asp | Ala | His | Ile | Ile | Gly | Arg | Ile | Glu | Ser | Tyr |
|---|---|---|---|---|---|---|---|---|---|---|---|---|---|---|---|
| | | | 20 | | | | | 25 | | | | | 30 | | |

| Ser | Cys | Lys | Met | Ala | Gly | Asp | Asp | Lys | His | Met | Phe | Lys | Gln | Phe | Cys |
|---|---|---|---|---|---|---|---|---|---|---|---|---|---|---|---|
| | | | 35 | | | | | 40 | | | | | 45 | | |

| Gln | Glu | Gly | Gln | Pro | His | Val | Leu | Glu | Ala | Leu | Ser | Pro | Pro | Gln | Thr |
|---|---|---|---|---|---|---|---|---|---|---|---|---|---|---|---|
| | 50 | | | | | 55 | | | | | 60 | | | | |

| Ser | Gly | Leu | Ser | Pro | Ser | Arg | Leu | Ser | Lys | Ser | Gln | Gly | Gly | Glu | Glu |
|---|---|---|---|---|---|---|---|---|---|---|---|---|---|---|---|
| 65 | | | | | 70 | | | | | 75 | | | | | 80 |

| Glu | Gly | Pro | Leu | Ser | Asp | Lys | Cys | Ser | Arg | Lys | Thr | Leu | Phe | Tyr | Leu |
|---|---|---|---|---|---|---|---|---|---|---|---|---|---|---|---|
| | | | | 85 | | | | | 90 | | | | | 95 | |

| Ile | Ala | Thr | Leu | Asn | Glu | Ser | Phe | Arg | Pro | Asp | Tyr | Asp | Phe | Ser | Thr |
|---|---|---|---|---|---|---|---|---|---|---|---|---|---|---|---|
| | | | 100 | | | | | 105 | | | | | 110 | | |

| Ala | Arg | Ser | His | Glu | Phe | Ser | Arg | Glu | Pro | Ser | Leu | Ser | Trp | Val | Val |
|---|---|---|---|---|---|---|---|---|---|---|---|---|---|---|---|
| | | | 115 | | | | | 120 | | | | | 125 | | |

| Asn | Ala | Val | Asn | Cys | Ser | Leu | Phe | Ser | Ala | Val | Arg | Glu | Asp | Phe | Lys |
|---|---|---|---|---|---|---|---|---|---|---|---|---|---|---|---|
| | 130 | | | | | 135 | | | | | 140 | | | | |

| Asp | Leu | Lys | Pro | Gln | Leu | Trp | Asn | Ala | Val | Asp | Glu | Glu | Ile | Cys | Leu |
|---|---|---|---|---|---|---|---|---|---|---|---|---|---|---|---|
| 145 | | | | | 150 | | | | | 155 | | | | | 160 |

| Ala | Glu | Cys | Asp | Ile | Tyr | Ser | Tyr | Asn | Pro | Asp | Leu | Asp | Ser | Asp | Pro |
|---|---|---|---|---|---|---|---|---|---|---|---|---|---|---|---|
| | | | | 165 | | | | | 170 | | | | | 175 | |

| Phe | Gly | Glu | Asp | Gly | Ser | Leu | Trp | Ser | Phe | Asn | Tyr | Phe | Phe | Tyr | Asn |
|---|---|---|---|---|---|---|---|---|---|---|---|---|---|---|---|
| | | | 180 | | | | | 185 | | | | | 190 | | |

| Lys | Arg | Leu | Lys | Arg | Ile | Val | Phe | Phe | Ser | Cys | Arg | Ser | Ile | Ser | Gly |
|---|---|---|---|---|---|---|---|---|---|---|---|---|---|---|---|
| | | | 195 | | | | | 200 | | | | | 205 | | |

| Ser | Thr | Tyr | Thr | Pro | Ser | Glu | Ala | Gly | Asn | Glu | Leu | Asp | Met | Glu | Leu |
|---|---|---|---|---|---|---|---|---|---|---|---|---|---|---|---|
| | 210 | | | | | 215 | | | | | 220 | | | | |

| Gly | Glu | Glu | Val | Glu | Glu | Ser | Arg | Ser | Arg | Gly | Ser | Gly | Ala |
|---|---|---|---|---|---|---|---|---|---|---|---|---|---|
| 225 | | | | | 230 | | | | | 235 | | | 240 |

| Glu | Glu | Thr | Ser | Thr | Met | Glu | Glu | Asp | Arg | Val | Pro | Val | Ile | Cys | Ile |
|---|---|---|---|---|---|---|---|---|---|---|---|---|---|---|---|
| | | | | 245 | | | | | 250 | | | | | 255 | |

<210> SEQ ID NO 2
<211> LENGTH: 922
<212> TYPE: PRT
<213> ORGANISM: Homo sapiens

<400> SEQUENCE: 2

| Glu | Asp | Val | Pro | Glu | Gly | Pro | Arg | Arg | Gly | Gly | Arg | Pro | Ser | Ala | Ala |
|---|---|---|---|---|---|---|---|---|---|---|---|---|---|---|---|
| 1 | | | | 5 | | | | | 10 | | | | | 15 | |

| Thr | Asp | Glu | Pro | Gly | Val | Thr | Asp | Phe | Arg | Pro | Thr | Ala | Glu | Ala | His |
|---|---|---|---|---|---|---|---|---|---|---|---|---|---|---|---|
| | | | 20 | | | | | 25 | | | | | 30 | | |

| Gln | Pro | Pro | Trp | Gly | Ser | Gln | Pro | Gln | Val | Pro | Trp | Arg | Pro | Ala | Gln |
|---|---|---|---|---|---|---|---|---|---|---|---|---|---|---|---|
| | | | 35 | | | | | 40 | | | | | 45 | | |

| Pro | Ser | Trp | Arg | Pro | Ser | Phe | Pro | Thr | Leu | Gly | Gly | Leu | Ala | Val |
|---|---|---|---|---|---|---|---|---|---|---|---|---|---|---|
| | 50 | | | | | 55 | | | | | 60 | | | | |

| Trp | Gly | Pro | Leu | Glu | Leu | Ile | Gln | Ala | Cys | Leu | Ser | Pro | Gly | Thr | Pro |
|---|---|---|---|---|---|---|---|---|---|---|---|---|---|---|---|
| 65 | | | | | 70 | | | | | 75 | | | | | 80 |

| Val | Trp | Gly | Trp | Ser | Leu | Ser | Gln | Pro | Leu | Pro | Gln | Pro | Thr | Gly | Met |
|---|---|---|---|---|---|---|---|---|---|---|---|---|---|---|---|
| | | | | 85 | | | | | 90 | | | | | 95 | |

| Pro | Pro | Ser | Ile | Pro | Pro | Val | Pro | Val | Pro | Val | Cys | Ser | Glu | Ala | Leu |
|---|---|---|---|---|---|---|---|---|---|---|---|---|---|---|---|
| | | | 100 | | | | | 105 | | | | | 110 | | |

| Ser | Leu | Ile | His | Arg | Arg | Arg | Ala | Thr | Ser | Gln | His | Leu | Val | Pro | Lys |

```
                    115                 120                 125
Glu Asp Leu Asp Ala Ile Val Ala Arg Asp Arg Asp Leu Gln Gln Leu
130                 135                 140

Arg Leu Gly Leu Val Val Pro Ala Ala Gln Pro Pro Ser Trp Gln
145                 150                 155                 160

Gln Arg Gln Glu Gly Phe Asp Asn Tyr Leu Arg Leu Ile Tyr Gly Ser
                    165                 170                 175

Gly Leu Leu Gly Met Gln Ser Gly Arg Gly Ser Gln Gln Trp Ser Ala
                180                 185                 190

Gly Thr Leu Arg Val Glu Arg Glu Thr Arg Asp Val Cys Ala Val Pro
            195                 200                 205

Gln Ala Ala His Cys Leu Ala Arg Ala Glu Val Ser Thr Ala Ala Gln
210                 215                 220

Thr Val Pro Thr Ala Leu Ser Pro Gln Asp Leu Gly Ala Leu Gly Gln
225                 230                 235                 240

His Phe Ser Gln Ser Pro Arg Val Thr Val Pro Ile Pro Pro Thr His
                245                 250                 255

Arg Arg Val His Ser Lys Ala Ser Gln Leu Leu Ala Arg Ser Ser Leu
                260                 265                 270

Ser His Tyr Leu Gly Ile Ser Leu Asp Leu Gln Leu Gln Leu Glu Gln
            275                 280                 285

Leu Arg Gly Arg Thr Thr Met Ala Leu Asp Leu Pro Ser Ser His Leu
290                 295                 300

Gln Cys Arg Ile Pro Leu Leu Pro Lys Arg Trp Asp Lys Glu Pro Leu
305                 310                 315                 320

Ser Ser Leu Arg Gly Phe Phe Pro Ala Thr Val Gln Pro His Lys His
                325                 330                 335

Cys Leu Arg Pro Ile Cys Phe Pro Gly Tyr Val Pro Asn Ser Ala Val
                340                 345                 350

Leu Gln Gln Met Trp Leu Asn Ala Glu Pro Gly Ala Ser Gln Asp Ala
            355                 360                 365

Leu Trp Leu Trp Arg Pro Arg Pro Ser Gln Ala Gln Trp Gln Arg Lys
370                 375                 380

Leu Leu Gln Trp Met Gly Glu Lys Pro Gly Glu Glu Gly Glu Glu Asp
385                 390                 395                 400

Lys Lys Glu Glu Glu Glu Lys Glu Asp Glu Glu Leu Asp Trp Ala
                405                 410                 415

Leu Ala Ser Leu Ser Pro His Ser Asn Gln Gln Leu Asp Ser Trp Glu
            420                 425                 430

Leu Glu Asp Gln Ser Ala Val Asp Trp Thr Gln Glu Pro Arg Arg Arg
435                 440                 445

Ser Cys Lys Val Ala Arg Thr His Pro His Pro Trp His Arg His Gly
450                 455                 460

Ser Leu Leu Leu Asp Glu His Tyr Gly His Leu Pro Lys Phe Leu His
465                 470                 475                 480

Phe Phe Ile Tyr Gln Thr Trp Phe Lys Lys Leu Phe Pro Ile Phe Ser
                485                 490                 495

Leu Gln Ala Tyr Pro Glu Ala Gly Thr Ile Glu Gly Leu Ala Ser Leu
            500                 505                 510

Leu Val Ala Leu Leu Glu Lys Thr Thr Trp Val Asp Arg Val His Ile
            515                 520                 525

Leu Gln Val Leu Leu Arg Leu Leu Pro Asn Met Ser Ser Asp Leu Gln
530                 535                 540
```

-continued

```
Gly Gln Leu Gln Gly Leu Leu Val His Leu Leu Asn Leu Asp Gln Pro
545                 550                 555                 560

Pro Ser Leu Gln Asp Gln Thr Gln Lys Lys Phe Val Ile Leu Ala Leu
                565                 570                 575

Gln Leu Leu Leu Ala Cys Ser Leu Glu Ser Arg Asp Val Val Leu Glu
                580                 585                 590

Leu Met Ser Tyr Phe Leu Tyr Ser Pro Val His Cys Arg Pro Glu Leu
            595                 600                 605

Lys Lys Leu Leu His Gly Leu Gly Leu Gln Asp Pro Glu Gly Phe Leu
        610                 615                 620

Phe Lys Glu Met Met Thr Trp Val Gln Gly Pro Asp Leu Asp Ser Lys
625                 630                 635                 640

Ala Gly Leu Arg Thr Cys Cys His Gln Lys Leu Glu Asp Met Ile Gln
                645                 650                 655

Glu Leu Gln Glu Thr Pro Ser Gln Thr Ser Val Val Ser Gly Ala Pro
                660                 665                 670

Thr Arg Ala Ser Val Ile Pro Ser Gly Thr Ser Trp Ser Ala Ser Gly
        675                 680                 685

Ile Phe Gly Arg Leu Ser Gln Val Ser Glu Val Pro Leu Met Val Val
        690                 695                 700

Ser Pro Ala Glu Pro His Ser Leu Ala Pro Glu Leu Gln Ala Gln Arg
705                 710                 715                 720

Met Leu Ala Pro Thr Arg Ser Trp Gly Thr Pro Gln Leu Arg Leu Arg
                725                 730                 735

Val Leu Ser Glu Thr Leu Lys Ser Phe Cys Leu Glu Pro Glu Ala Arg
            740                 745                 750

Leu His Pro Ala Gly Pro Ala Gln Leu Pro Gly Glu Pro Pro Pro Leu
        755                 760                 765

Glu Glu Thr Asp Trp Ser His Ser Gln Leu Leu Asp Leu Gly Pro Ile
770                 775                 780

Asp Ala Leu Asn Phe Phe Cys Glu Gln Leu Arg Ala Gln Arg Ser
785                 790                 795                 800

Ser Leu Gln Glu Lys Ala Ala His Pro His Pro Pro Val Pro Tyr Thr
                805                 810                 815

Val Ala Pro Val Pro Asp Met Val Val Pro Pro Arg Glu His Trp
                820                 825                 830

Tyr His Pro Ile Leu Arg Leu Gln Glu Ala Lys Pro Gln Arg Ser Ala
        835                 840                 845

Arg Ser Ala Met Arg Leu Arg Gly Pro Met Pro Ser Arg Leu Cys Ala
850                 855                 860

Gly Arg Thr Leu Asp Gly Pro Ile Arg Thr Leu Lys Leu Pro Leu Pro
865                 870                 875                 880

Arg Val Glu Pro Gln Pro Phe Pro Leu Asp Trp Pro Met Pro Pro Arg
                885                 890                 895

Pro Leu Pro Pro Arg Leu Leu Gln Pro Ala Leu Gln Arg Tyr Phe Leu
                900                 905                 910

Pro Ala Asp Ala Asp Pro Asp Thr Tyr Ser
                915                 920
```